(12) United States Patent
Perrin et al.

(10) Patent No.: US 11,069,056 B2
(45) Date of Patent: Jul. 20, 2021

(54) MULTI-MODAL COMPUTER-AIDED DIAGNOSIS SYSTEMS AND METHODS FOR PROSTATE CANCER

(71) Applicant: General Electric Company, Schenectady, NY (US)

(72) Inventors: Baptiste Maurice Perrin, Buc (FR); Melodie Sperandio, Buc (FR); Lucile Nosjean, Buc (FR); Lorraine Jammes, Buc (FR)

(73) Assignee: General Electric Company, Schenectady, NY (US)

( * ) Notice: Subject to any disclaimer, the term of this patent is extended or adjusted under 35 U.S.C. 154(b) by 73 days.

(21) Appl. No.: 16/196,887

(22) Filed: Nov. 20, 2018

(65) Prior Publication Data

US 2019/0156477 A1     May 23, 2019

Related U.S. Application Data

(60) Provisional application No. 62/590,266, filed on Nov. 22, 2017.

(51) Int. Cl.
*G06K 9/00*     (2006.01)
*G06T 7/00*     (2017.01)
(Continued)

(52) U.S. Cl.
CPC .......... *G06T 7/0012* (2013.01); *A61B 5/055* (2013.01); *G01N 33/57434* (2013.01); *G16H 15/00* (2018.01); *G16H 30/20* (2018.01); *G16H 30/40* (2018.01); *G16H 40/63* (2018.01); *G16H 50/20* (2018.01); *G16H 50/30* (2018.01);
(Continued)

(58) Field of Classification Search
None
See application file for complete search history.

(56) References Cited

U.S. PATENT DOCUMENTS 9,678,190 B2   6/2017   Koch
2006/0030768 A1*   2/2006   Ramamurthy ............ G06T 7/38
                                                                600/407
(Continued)

OTHER PUBLICATIONS

Peng, Yahui, et al. "MRI-based prostate volume-adjusted prostate-specific antigen in the diagnosis of prostate cancer." Journal of Magnetic Resonance Imaging 42.6 (2015): 1733-1739. (Year: 2015).*
(Continued)

*Primary Examiner* — Sean M Conner

(57) ABSTRACT

Methods and apparatus for computer-aided prostate condition diagnosis are disclosed. An example computer-aided prostate condition diagnosis apparatus includes a memory to store instructions and a processor. The example processor is to execute the instructions to implement at least a prostate assessor, a lesion assessor, and an outcome generator. The example prostate assessor is to evaluate a volume and density of a prostate gland in an image of a patient to determine a prostate-specific antigen level for the prostate gland. The example lesion assessor is to analyze a lesion on the prostate gland in the image. The example outcome generator is to generate an assessment of prostate gland health based on the prostate-specific antigen level and the analysis of the lesion.

20 Claims, 25 Drawing Sheets

(51) Int. Cl.
    *G01N 33/574*    (2006.01)
    *A61B 5/055*     (2006.01)
    *G16H 50/20*     (2018.01)
    *G16H 30/20*     (2018.01)
    *G16H 30/40*     (2018.01)
    *G16H 50/30*     (2018.01)
    *G16H 15/00*     (2018.01)
    *G16H 40/63*     (2018.01)

(52) U.S. Cl.
    CPC .............. *G06T 2207/10096* (2013.01); *G06T 2207/30081* (2013.01); *G06T 2207/30096* (2013.01)

(56) References Cited

U.S. PATENT DOCUMENTS

| | | | | |
|---|---|---|---|---|
| 2009/0176218 | A1* | 7/2009 | Cheng | C12Q 1/6886 435/6.14 |
| 2010/0177950 | A1* | 7/2010 | Donovan | G16H 50/20 382/133 |
| 2011/0158491 | A1* | 6/2011 | Markova | G06T 7/41 382/128 |
| 2011/0170755 | A1* | 7/2011 | Buelow | G06T 7/0012 382/128 |
| 2013/0034282 | A1* | 2/2013 | Kaufman | G06T 7/0014 382/128 |
| 2016/0217262 | A1* | 7/2016 | Sharbell | G16H 50/20 |
| 2018/0024995 | A1* | 1/2018 | Choi | G06K 9/6211 707/736 |

OTHER PUBLICATIONS

Tian, Zhiqiang, Lizhi Liu, and Baowei Fei. "Deep convolutional neural network for prostate MR segmentation." Medical Imaging 2017: Image-Guided Procedures, Robotic Interventions, and Modeling. vol. 10135. International Society for Optics and Photonics, 2017. (Year: 2017).*

Datta, Shoumen Palit Austin. "Emergence of digital twins." arXiv preprint arXiv:1610.06467 (2016). (Year: 2016).*

International Searching Authority, "Search Report and Written Opinion," issued in connection with International Patent Application No. PCT/US2018/062130, dated Feb. 25, 2019, 14 pages.

Bjurlin, et al., "MRI of the Prostate, Standard Operating Procedure (SOP)," May 8, 2017, available at [https://web.archive.org/web/20170508165143/https://www.auanet.org/guidelines/mri-of-the-prostate-sop], 22 pages.

Corcoran, et al., "The ability of prostate-specific antigen (PSA) density to predict an upgrade in Gleason score between initial prostate biopsy and prostatectomy diminishes with increasing tumour grade due to reduced PSA secretion per unit tumour volume," BJU International, vol. 110, No. 1, Jul. 1, 2012, pp. 36-42.

Varkarakis, et al., "Measurement of PSA density by 3 imaging modalities and its correlation with the PSA density of radical prostatectomy specimen," Urologic Oncology: Seminars and Original Investigations, vol. 31, No. 7, Oct. 1, 2013, pp. 1038-1042.

* cited by examiner

Name: DEMO_PROSTATE_WITH_ADC  
Birth Date:  
ID: AW1466415397.76.1488973432  
Study Date:  
Hospital Name:

Patient Clinical History

PSA level increased from 3 to 7 between July 2016 and December 2016 [...]

Prostate Gland Volume: 125.72 cm³  
Dist1 : 51.0 mm  
Dist2 : 69.1 mm  
Dist3 : 68.5 mm

PSA Level: 7 ng/ml  
PSA Density: 0.06 ng/ml²

Details of Lesion(s)

| MR Tech / Findings | PI-RADS Score * | | | | MR - ADC (mm²/s) [1] / MR - ADC (10^-6 mm²/s) [2] | | | Length | volume | Extra prostatic extension ? |
|---|---|---|---|---|---|---|---|---|---|---|
| | T2 | DWI | DCE | Overall | Min | Avg | Stdev | | | |
| Lesion 2 (Index Lesion) Main Zone: PZ | 4 | 5 | - | 5 | 0.000356 [1] | 0.00191 [1] | 0.000662 [1] | 23.6 mm | | Yes |
| Lesion 1 Main Zone: TZ | 3 | 2 | + | 3 | 0.000626 [1] | 0.0014 [1] | 0.000425 [1] | 16.4 mm | | No |

FIG. 19A

MULTI-MODAL COMPUTER-AIDED DIAGNOSIS SYSTEMS AND METHODS FOR PROSTATE CANCER

CROSS-REFERENCE TO RELATED APPLICATION

This patent arises from U.S. Provisional Patent Application Ser. No. 62/590,266, which was filed on Nov. 22, 2017. U.S. Provisional Patent Application Ser. No. 62/590,266 is hereby incorporated herein by reference in its entirety. Priority to U.S. Provisional Patent Application Ser. No. 62/590,266 is hereby claimed.

FIELD OF THE DISCLOSURE

This disclosure relates generally to improved medical systems and, more particularly, to improved computer-aided diagnosis systems and methods for medical image processing.

BACKGROUND

A variety of economy, technological, and administrative hurdles challenge healthcare facilities, such as hospitals, clinics, doctors' offices, etc., to provide quality care to patients. Economic drivers, less skilled staff, fewer staff, complicated equipment, and emerging accreditation for controlling and standardizing radiation exposure dose usage across a healthcare enterprise create difficulties for effective management and use of imaging and information systems for examination, diagnosis, and treatment of patients.

Healthcare provider consolidations create geographically distributed hospital networks in which physical contact with systems is too costly. At the same time, referring physicians want more direct access to supporting data in reports along with better channels for collaboration. Physicians have more patients, less time, and are inundated with huge amounts of data, and they are eager for assistance.

Healthcare provider tasks including image processing and analysis, etc., are time consuming and resource intensive tasks impractical, if not impossible, for humans to accomplish alone.

BRIEF DESCRIPTION

Certain examples provide a computer-aided prostate condition diagnosis apparatus. The example apparatus includes a memory to store instructions and a processor. The example processor is to execute the instructions to implement at least a prostate assessor, a lesion assessor, and an outcome generator. The example prostate assessor is to evaluate a volume and density of a prostate gland in an image of a patient to determine a prostate-specific antigen level for the prostate gland. The example lesion assessor is to analyze a lesion on the prostate gland in the image. The example outcome generator is to generate an assessment of prostate gland health based on the prostate-specific antigen level and the analysis of the lesion.

Certain examples provide a computer-readable storage medium including instructions. The instructions, when executed, cause at least one processor to at least: evaluate a volume and density of a prostate gland in an image of a patient to determine a prostate-specific antigen level for the prostate gland; analyze a lesion on the prostate gland in the image; and generate an assessment of prostate gland health based on the prostate-specific antigen level and the analysis of the lesion.

Certain examples provide a method for computer-aided prostate condition diagnosis. The example method includes evaluating, with at least one processor, a volume and density of a prostate gland in an image of a patient to determine a prostate-specific antigen level for the prostate gland. The example method includes analyzing, with the at least one processor, a lesion on the prostate gland in the image. The example method includes generating, with the at least one processor, an assessment of prostate gland health based on the prostate-specific antigen level and the analysis of the lesion.

BRIEF DESCRIPTION OF THE DRAWINGS

FIGS. 11-19C depict example interfaces facilitate prostate analysis and associated patient diagnosis and treatment.

Figure 1A:
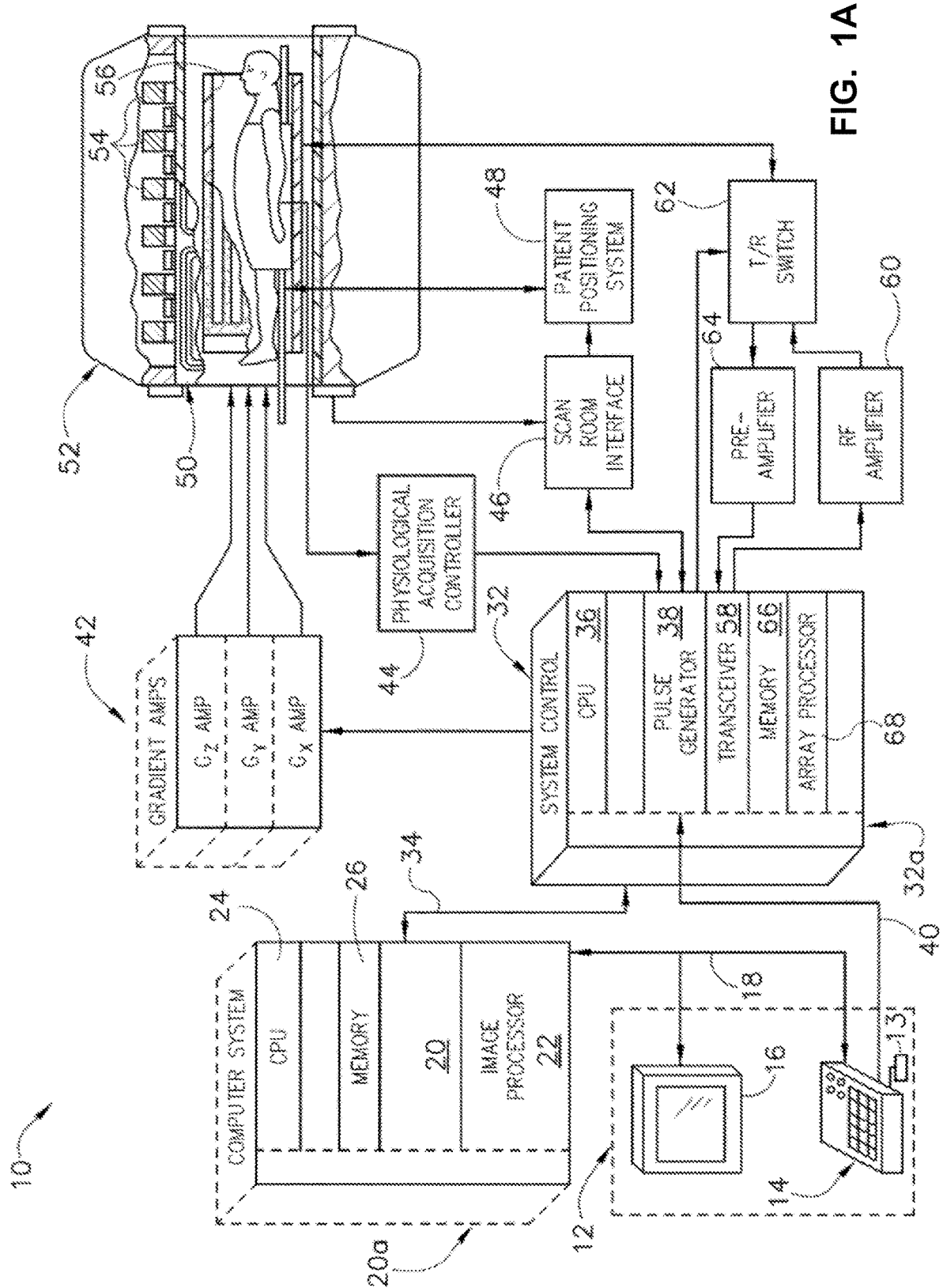
FIG. 1A illustrates an example imaging system to which the methods, apparatus, and articles of manufacture disclosed herein can be applied.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings. The figures are not scale. Wherever possible, the same reference numbers will be used throughout the drawings and accompanying written description to refer to the same or like parts.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

In addition, it should be understood that references to "one embodiment" or "an embodiment" of the present disclosure are not intended to be interpreted as excluding the existence of additional embodiments that also incorporate the recited features.

Overview

Imaging devices (e.g., gamma camera, positron emission tomography (PET) scanner, computed tomography (CT) scanner, X-Ray machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. MR, for example, is a medical imaging modality that generates images of the inside of a human body without using x-rays or other ionizing radiation. MR uses a main magnet to create a strong, uniform, static magnetic field (e.g., the "main magnetic field") and gradient coils to produce smaller amplitude, spatially varying magnetic fields when a current is applied to the gradient coils. When a human body, or part of a human body, is placed in the main magnetic field, the nuclear spins that are associated with hydrogen nuclei in tissue water become polarized. The magnetic moments that are associated with these spins become preferentially aligned along the direction of the main magnetic field, resulting in a small net tissue magnetization along that axis (the "z axis," by convention) and the gradient coils encode the MR signal.

Acquisition, processing, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine learning, deep learning, and/or other artificial intelligence can be used to help configure, monitor, and update the medical imaging workflow and devices, for example.

Certain examples provide and/or facilitate improved imaging devices which improve diagnostic accuracy and/or coverage. Certain examples facilitate improved image reconstruction and further processing to provide improved diagnostic accuracy.

Certain examples provide improved management and analysis of medical images including MR images to which computer-aided diagnosis (CAD) and/or other artificial intelligence can be applied to identify and classify anomalies/abnormalities such as prostate cancer, etc.

Certain examples improve MR imaging and image data processing technology to enable an automated multi-part clinical analysis performing oncological scoring and CAD resulting in a patient disease (e.g., prostate cancer, etc.) determination and routing/reporting to another clinical system, specialist, medical record, etc. Certain examples provide technological improvements to automate processing such as image segmentation, oncology scoring, report generation, etc., to reduce, minimize, or eliminate user interaction in the detection/diagnosis process.

Certain examples gather patient history and evaluate the patient's prostate-specific antigen (PSA) level based on blood test data. PSA is a substance produced by the prostate gland, and elevated PSA levels may indicate prostate cancer or a non-cancerous condition such as an enlarged prostate, for example. Using image data (e.g., axial, sagittal, etc.), apparent diffusion coefficient (ADC) blood flow mapping information, etc., prostate gland volume and PSA density can be computed by the system, for example. Then, using computer-aided detection and/or user input, lesions can be identified with respect to the patient's prostate gland using the image data, ADC information, density, segmentation, and/or other automated image data analysis, for example. Regions of interest (ROIs) can be defined around identified, possible, and/or likely lesions to mark lesion(s) in the image(s). Lesions in the ROIs can then be segmented by the system (e.g., along a long axis, etc.) and scored (e.g., to determine a likelihood of lesion verification, malignancy/severity, size, etc.), for example. Deep learning, machine learning, and/or other artificial intelligence can be used to automatically segment and compute prostate volume and/or to automatically segment, locate, and score lesion(s) in/on the prostate gland, for example. A determination of likely prostate cancer, trigger for patient care plan/treatment, report for urologist and/or other clinician, etc., can be generated with score, lesion detail, observation, comment, conclusion, etc.

An apparent diffusion coefficient (ADC) image or an ADC map is an MR image that more specifically shows diffusion than conventional diffusion weighted imaging (DWI), by eliminating certain (e.g., T2) weighing that is otherwise inherent in conventional DWI. ADC imaging does so by acquiring multiple conventional DWI images with different amounts of DWI weighing, and the change in signal is proportional to the rate of diffusion.

A score, such as a pirads or pi-rads score, can represent an indication of likely cancerous/tumor tissue, for example. PI-RADS is an acronym for Prostate Imaging Reporting and Data System, defining quality standards for multi-parametric MR imaging including image creation and reporting. A PI-RADS score is provided for each variable parameter along a scale based on a score of "yes" or "no for a dynamic contrast-enhanced (DCE or Dice) parameter, from 1 to 5 for T2-weighted (T2 W) and diffusion-weighted imaging (DWI), for example. The score is determined for each detected lesion, with 1 being most probably benign and 5 being highly suspicious of malignancy. For example, pirads 1 is "very low" (e.g., clinically significant cancer is highly unlikely to be present); pirads 2 is "low" (e.g., clinically significant cancer is unlikely to be present); pirads 3 is "intermediate" (e.g., the presence of clinically significant cancer is equivocal); pirads 4 is "high" (e.g., clinically significant cancer is likely to be present); and pirads 5 is "very high" (e.g., clinically significant cancer is highly likely to be present).

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Example Magnetic Resonance Imaging System

Turning to FIG. 1A, the major components of an exemplary magnetic resonance imaging (MRI) system 10 are shown. Operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26 that may include a frame buffer for storing image data arrays. The computer system 20 is linked to archival media devices, permanent or back-up memory storage or a network for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. The pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

Gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. In an embodiment of the invention, RF coil 56 is a multi-channel coil. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

MR signals received/detected by the multi-channel RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12, this image data may be archived in long term storage or it may be further processed by the image processor 22 and conveyed to the operator console 12 and presented on the display 16.

Example Computer-Aided Prostate Analysis System

Figure 1B:
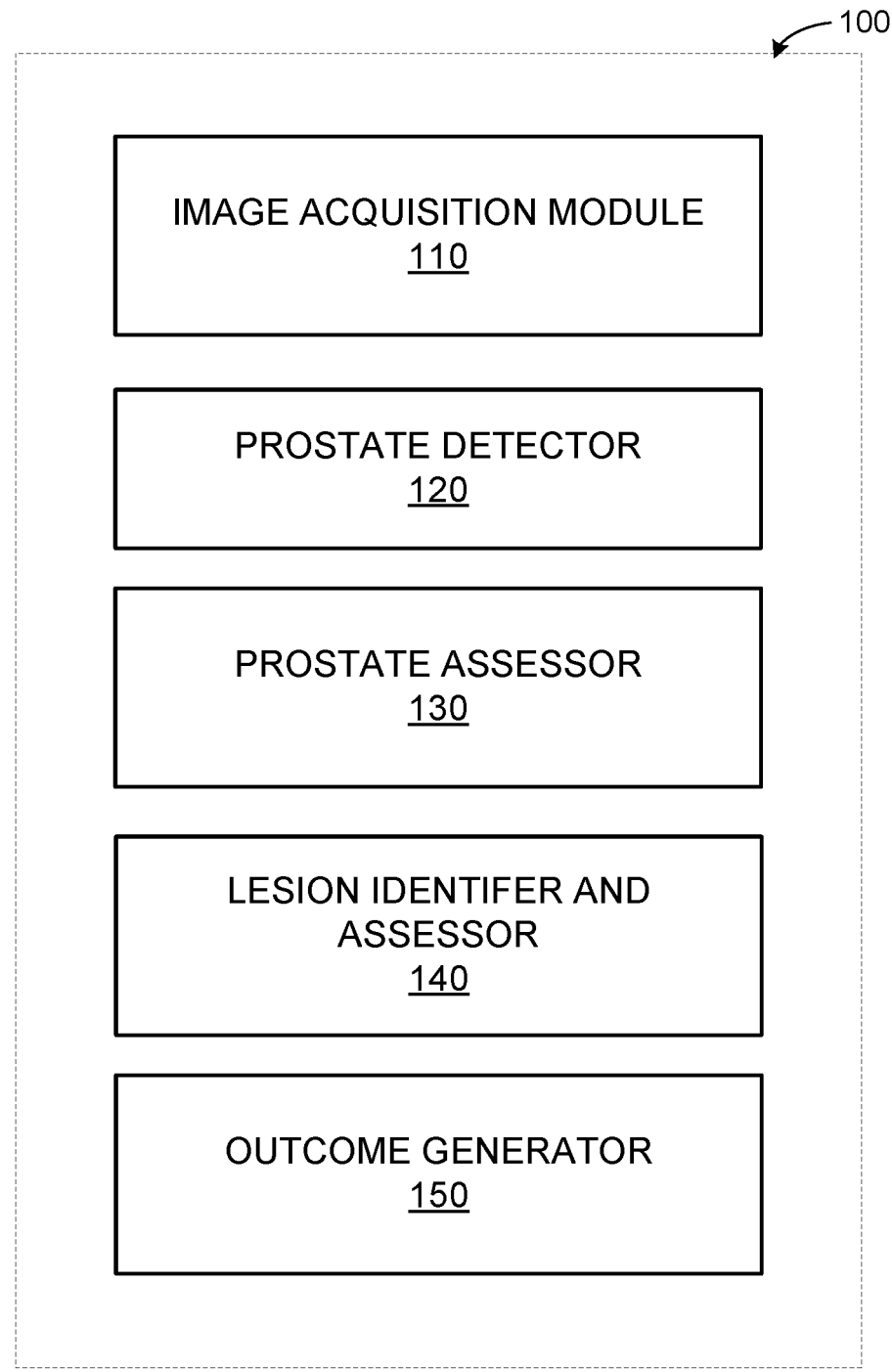
FIG. 1B illustrates an example computer-aided prostate analysis system.

FIG. 1B illustrates an example computer-aided prostate analysis system 100 including an image acquisition module 110, a prostate detector 120, a prostate assessor 130, a lesion identifier and assessor 140 (also referred to herein as a lesion assessor), and an outcome generator 150.

The example system 100 enables computer-assisted diagnostics and classification of prostate cancer. Certain examples analyze prostate information and generate a prediction and/or other analysis regarding likely prostate cancer, malignant lesion, and/or other prostate issue. For example, certain examples position a prostate lesion on a prostate sector map using multimodal multi-protocol MR data and integrate prostate lesion information for a computer-aided diagnosis and classification system for prostate cancer.

The example image acquisition module 110 acquires image data, such as an ADC image, DWI image, and/or other MR image data, etc., for a patient. The image data includes the patient's prostate gland, for example. The image acquisition module 110 can preprocess the image data to prepare it for further analysis, for example. For example, contrast, window level, etc., can be adjusted to accentuate the prostate gland in the image data, etc.

The example prostate detector 120 processes the image data to identify the prostate gland in the image. For example, based on pixel density/intensity values, the prostate detector 120 can identify the prostate gland in the image data. In other examples, the image can be segmented and scored to identify and register the prostate gland in the image (e.g., an MR image, 3D volume, etc.).

The example prostate assessor 130 processes the image data in conjunction with patient clinical history information and determines a prostate-specific antigen (PSA) level for the patient. An elevated PSA level, indicating a greater than normal presence of prostate-specific antigen in the patient's blood stream, can be an indicator of prostate cancer in the associated patient. The prostate assessor 130 can segment the prostate in the image and compute its volume (e.g., using deep learning-based methods, etc.), for example. For example, the prostate assessor 130 can deposit distances (e.g., 3 distances, etc.) on the image (e.g., using a dedicated distance tool, etc.) and prostate volume and PSA density can be computed automatically.

The example lesion identifier and assessor MO identifies and processes a lesion on the image data. For example, the lesion identifier and assessor 140 can identify and process a lesion in the image by depositing a graphical object (e.g., indicating a region of interest (e.g., along its long axis, etc.), etc.) on a lesion in one or more acquired images. For example, an ellipse is deposited on a prostate sector map, with schema and sector(s) underneath the map automatically selected (e.g., ellipses are deposited on axial, sagittal, and coronal planes to automatically select corresponding sectors, etc.). The lesion can then be scored by the lesion identifier and assessor MO according to PIRADS v2 guidelines. In another example, lesion(s) are automatically segmented and then located and scored for each available MR imaging technique (e.g., using non-rigid registration of the segmented prostate and a 3D model of the prostate sector map and deep learning based methods, etc.). A global score, for example, can be automatically computed from the various MR technique lesion scores. As another example, lesion(s) are identified using available tools, algorithms, digital twin, etc.

From the lesion information, a conclusion, recommendation, and/or other evaluation regarding likely prostate issue(s) can be determined. Qualitative evaluation, hidden layer processing in a deep neural network, and an analysis of edges, edge combination(s), object models, etc., enable the deep neural network to correlate MR image data with likely prostate lesions and/or other imperfections necessitating follow-up for further verification, treatment, etc. Convolution, deconvolution, forward inference and backward learning from image segmentation and pixel intensity data can help drive a correlation between MR image information and likely prostate cancer determination via CAD, for example.

Based on the lesion analysis, a report and/or next action trigger can be generated and exported by the example outcome generator 150. For example, a report can be generated, saved, output, transferred, etc. For example, patient clinical history (e.g., including an identified trend in PSA level, etc.), prostate gland volume, PSA level, PSA density, lesion details, index lesion, comments, PI-RADS assessment, conclusion, etc., can be provided (e.g., transmitted to another program, trigger another process, saved, displayed, and/or otherwise output) based on the analysis to drive further action with respect to the patient.

Digital Twin Example

In certain examples, a digital representation of the patient, patient anatomy/region (e.g., prostate gland, etc.) can be used for computer-aided detection and/or diagnosis of prostate cancer. A digital representation, digital model, digital "twin", or digital "shadow" is a digital informational construct about a physical system, process, etc. That is, digital information can be implemented as a "twin" of a physical device/system/person/process and information associated with and/or embedded within the physical device/system/process. The digital twin is linked with the physical system through the lifecycle of the physical system. In certain examples, the digital twin includes a physical object in real space, a digital twin of that physical object that exists in a virtual space, and information linking the physical object with its digital twin. The digital twin exists in a virtual space corresponding to a real space and includes a link for data flow from real space to virtual space as well as a link for information flow from virtual space to real space and virtual sub-spaces.

Figure 2:
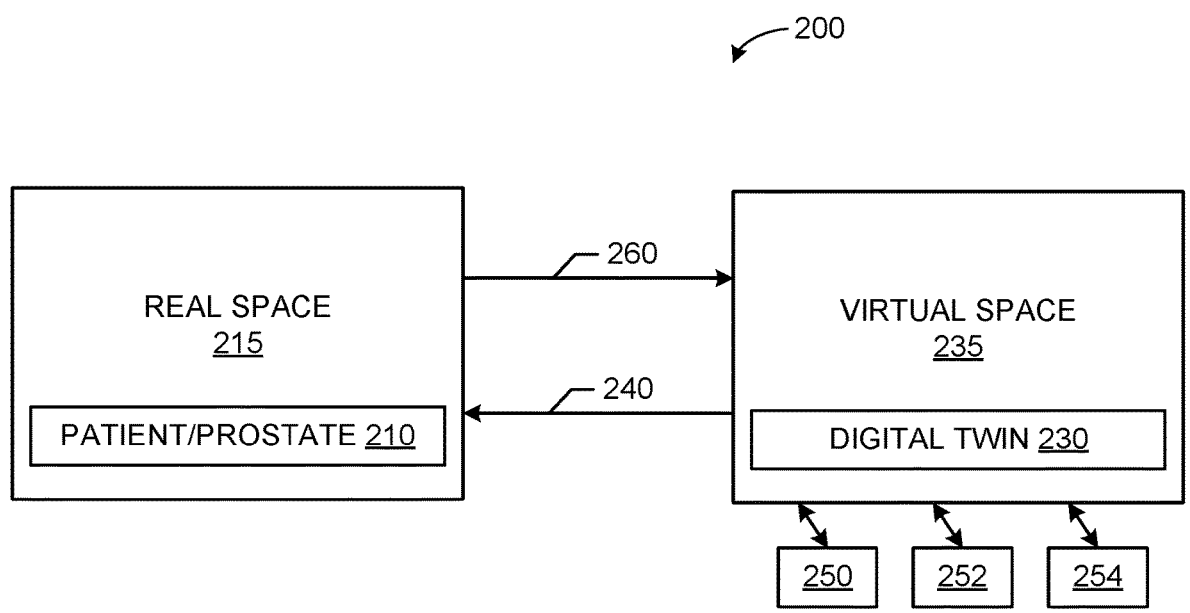
FIG. 2 depicts an example digital twin environment.

For example, FIG. 2 illustrates a patient, prostate gland, and/or other anatomy/anatomical region 210 in a real space 215 providing data 220 to a digital twin 230 in a virtual space 235. The digital twin 230 and/or its virtual space 235 provide information 240 back to the real space 215. The digital twin 230 and/or virtual space 235 can also provide information to one or more virtual sub-spaces 250, 252, 254. As shown in the example of FIG. 2, the virtual space 235 can include and/or be associated with one or more virtual sub-spaces 250, 252, 254, which can be used to model one or more parts of the digital twin 230 and/or digital "sub-twins" modeling subsystems/subparts of the overall digital twin 230.

Sensors connected to the physical object (e.g., the patient 210) can collect data and relay the collected data 220 to the digital twin 230 (e.g., via self-reporting, using a clinical or other health information system such as a picture archiving and communication system (PACS), radiology information system (RIS), electronic medical record system (EMR), laboratory information system (LIS), cardiovascular information system (CVIS), hospital information system (HIS), MR imaging scanner, and/or combination thereof, etc.). Interaction between the digital twin 230 and the patient/prostate 210 can help improve diagnosis, treatment, health maintenance, etc., for the patient 210 (such as identification of prostate issues, etc.), for example. An accurate digital description 230 of the patient/prostate 210 benefiting from a real-time or substantially real-time (e.g., accounting from data transmission, processing, and/or storage delay) allows the system 200 to predict "failures" in the form of disease, body function, and/or other malady, condition, etc.

In certain examples, obtained images overlaid with sensor data, lab results, etc., can be used in augmented reality (AR) applications when a healthcare practitioner is examining, treating, and/or otherwise caring for the patent 210. Using AR, the digital twin 230 follows the patient's response to the interaction with the healthcare practitioner, for example. Thus, the patient's prostate can be modeled to identify a change in appearance, lab results, scoring, and/or other characteristic to indicate a prostate issue such as cancer, evaluate the issue, model/predict treatment options, etc.

Thus, rather than a generic model, the digital twin 230 is a collection of actual physics-based, anatomically-based, and/or biologically-based models reflecting the patient/prostate 210 and his or her associated norms, conditions, etc. In certain examples, three-dimensional (3D) modeling of the patient/prostate 210 creates the digital twin 230 for the patient/prostate 210. The digital twin 230 can be used by the prostate assessor 130, for example, to determine (e.g., model, simulate, extrapolate, etc.) and view a status of the patient/prostate 210 based on input data 220 dynamically provided from a source (e.g., from the patient 210, imaging system, practitioner, health information system, sensor, etc.).

In certain examples, the digital twin 230 of the patient/prostate 210 can be used by the prostate assessor 130 for monitoring, diagnostics, and prognostics for the patient/prostate 210. Using sensor data in combination with historical information, current and/or potential future conditions of the patient/prostate 210 can be identified, predicted, monitored, etc., using the digital twin 230. Causation, escalation, improvement, etc., can be monitored via the digital twin 230. Using the digital twin 230, the patient/prostate's 210 physical behaviors can be simulated and visualized for diagnosis, treatment, monitoring, maintenance, etc.

In contrast to computers, humans do not process information in a sequential, step-by-step process. Instead, people try to conceptualize a problem and understand its context. While a person can review data in reports, tables, etc., the person is most effective when visually reviewing a problem and trying to find its solution. Typically, however, when a person visually processes information, records the information in alphanumeric form, and then tries to re-conceptualize the information visually, information is lost and the problem-solving process is made much less efficient over time.

Using the digital twin 230, however, allows a person and/or system to view and evaluate a visualization of a situation (e.g., a patient/prostate 210 and associated patient problem, etc.) without translating to data and back. With the digital twin 230 in common perspective with the actual patient/prostate 210, physical and virtual information can be viewed together, dynamically and in real time (or substantially real time accounting for data processing, transmission, and/or storage delay). Rather than reading a report, a healthcare practitioner can view and simulate with the digital twin 230 to evaluate a condition, progression, possible treatment, etc., for the patient/prostate 210. In certain examples, features, conditions, trends, indicators, traits, etc., can be tagged and/or otherwise labeled in the digital twin 230 to allow the practitioner to quickly and easily view designated parameters, values, trends, alerts, etc.

The digital twin 230 can also be used for comparison (e.g., to the patient/prostate 210, to a "normal", standard, or reference patient, set of clinical criteria/symptoms, best practices, protocol steps, etc.). In certain examples, the digital twin 230 of the patient/prostate 210 can be used to measure and visualize an ideal or "gold standard" value state for that patient/protocol/item, a margin for error or standard deviation around that value (e.g., positive and/or negative deviation from the gold standard value, etc.), an actual value, a trend of actual values, etc. A difference between the actual value or trend of actual values and the gold standard (e.g., that falls outside the acceptable deviation) can be visualized as an alphanumeric value, a color indication, a pattern, etc.

Further, the digital twin 230 of the patient 210 can facilitate collaboration among friends, family, care providers, etc., for the patient 210. Using the digital twin 230, conceptualization of the patient 210 and his/her health can be shared (e.g., according to a care plan, etc.) among multiple people including care providers, family, friends, etc. People do not need to be in the same location as the patient 210, with each other, etc., and can still view, interact with, and draw conclusions from the same digital twin 230, for example.

Thus, the digital twin 230 can be defined as a set of virtual information constructs that describes (e.g., fully describes) the patient 210 from a micro level (e.g., heart, lungs, foot, prostate gland, anterior cruciate ligament (ACL), stroke history, etc.) to a macro level (e.g., whole anatomy, holistic view, skeletal system, nervous system, vascular system, etc.). Similarly, the digital twin 230 can represent an item and/or a protocol at various levels of detail such as macro, micro, etc. In certain examples, the digital twin 230 can be a reference digital twin (e.g., a digital twin prototype, etc.) and/or a digital twin instance. The reference digital twin represents a prototypical or "gold standard" model of the patient/prostate 210 or of a particular type/category of patient/prostate 210, while one or more reference digital twins represent particular patient(s)/prostate(s) 210. Thus, the digital twin 230 of a child patient 210 may be implemented as a child reference digital twin organized according to certain standard or "typical" child characteristics, with a particular digital twin instance representing the particular child patient 210. In certain examples, multiple digital twin instances can be aggregated into a digital twin aggregate (e.g., to represent an accumulation or combination of multiple child patients sharing a common reference digital twin, etc.). The digital twin aggregate can be used to identify differences, similarities, trends, etc., between children represented by the child digital twin instances, for example.

In certain examples, the virtual space 235 in which the digital twin 230 (and/or multiple digital twin instances, etc.) operates is referred to as a digital twin environment. The digital twin environment 235 provides an integrated, multi-domain physics- and/or biologics-based application space in which to operate the digital twin 230. The digital twin 230 can be analyzed in the digital twin environment 235 to predict future behavior, condition, progression, etc., of the patient/protocol/item 210, for example. The digital twin 230 can also be interrogated or queried in the digital twin environment 235 to retrieve and/or analyze current information 240, past history, etc.

In certain examples, the digital twin environment 235 can be divided into multiple virtual spaces 250-254. Each virtual space 250-254 can model a different digital twin instance and/or component of the digital twin 230 and/or each virtual space 250-254 can be used to perform a different analysis, simulation, etc., of the same digital twin 230. Using the multiple virtual spaces 250-254, the digital twin 230 can be tested inexpensively and efficiently in a plurality of ways while preserving patient 210 safety. A healthcare provider can then understand how the patient/prostate 210 may react to a variety of treatments in a variety of scenarios, for example. Continuous, triggered, periodic, and/or other input 260 from the real space to the virtual space enables the digital twin 230 to continue to evolve.

Example Deep Learning and Other Machine Learning

Deep learning is a class of machine learning techniques employing representation learning methods that allows a machine to be given raw data and determine the representations needed for data classification. Deep learning ascertains structure in data sets using back propagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, identification of lesions in image data, computer-aided diagnosis (CAD), etc.

High quality medical image data can be acquired using one or more imaging modalities, such as x-ray, computed tomography (CT), molecular imaging and computed tomography (MET), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. For example, the lesion identifier and assessor 140 can use a deep learning network model to analyze lesion data identified in an image. The prostate assessor 130 can utilize a deep learning network model to evaluate prostate health based on an identified prostate gland in an image and associated patient health information, for example. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning. In certain examples, the digital twin 230 (e.g., as a whole and/or in one of its sub-parts 250-254) can leverage a deep learning network model to model behavior of a component, such as a prostate gland, lesion, other organ, etc.

Example Learning Network Systems

Figure 3:
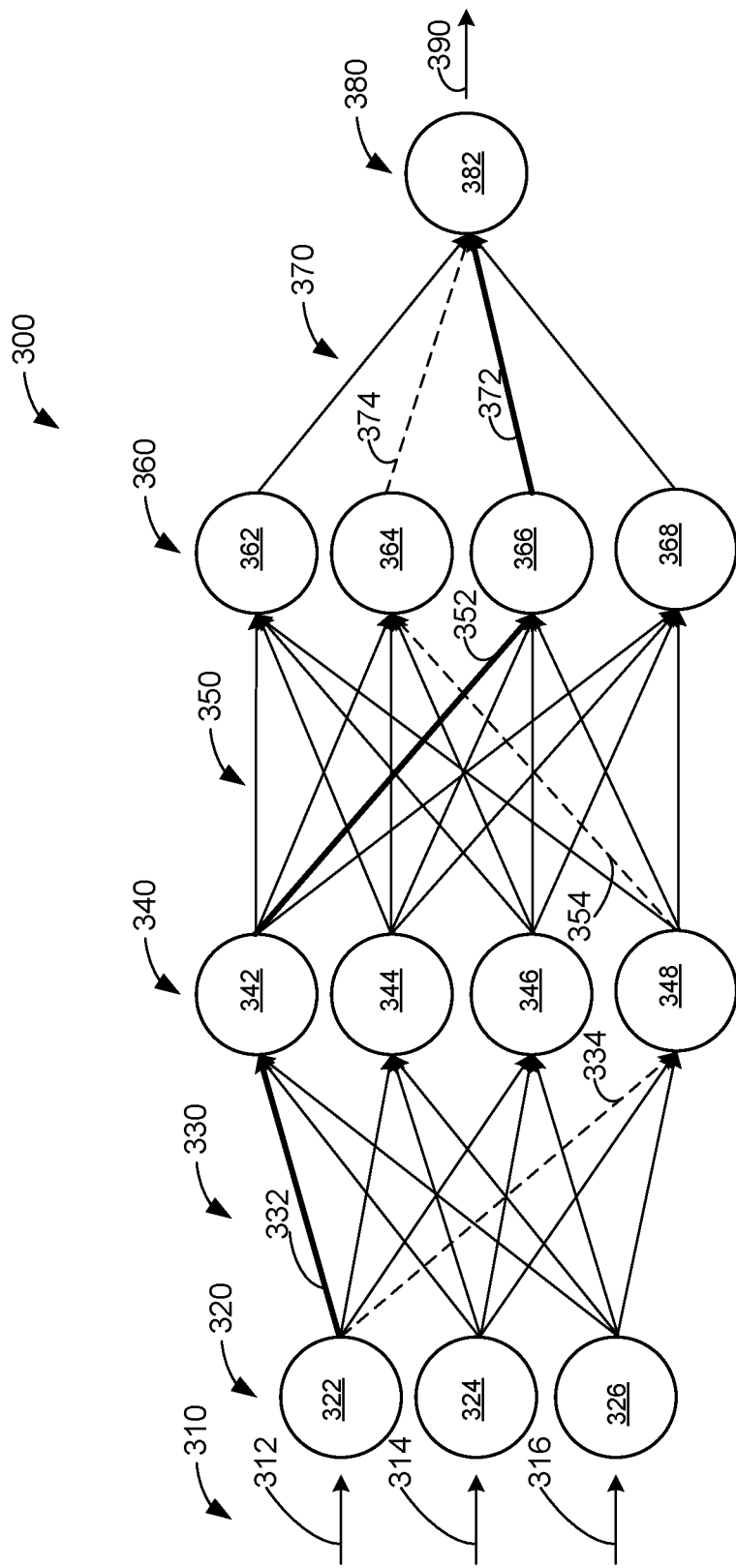
FIG. 3 is a representation of an example learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 and to an output 390.

The layer 320 is an input layer that, in the example of FIG. 3, includes a plurality of nodes 322, 324, 326. The layers 340 and 360 are hidden layers and include, the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370 certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Figure 4:
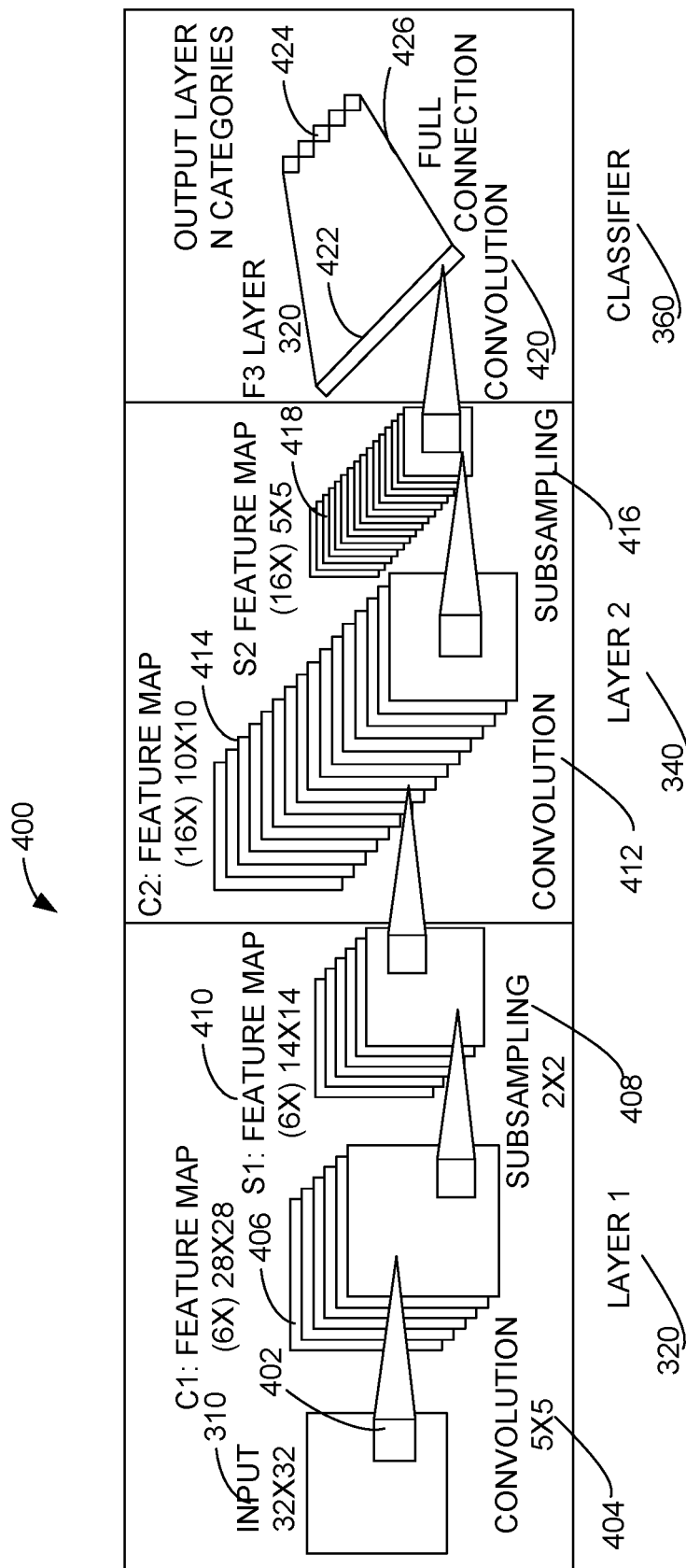
FIG. 4 illustrates a particular implementation of the example neural network as a convolutional neural network.

FIG. 4 illustrates a particular implementation of the example neural network 300 as a convolutional neural network 400. As shown in the example of FIG. 4, an input 310 is provided to the first layer 320 which processes and propagates the input 310 to the second layer 340. The input 310 is further processed in the second layer 340 and propagated to the third layer 360. The third layer 360 categorizes data to be provided to the output layer e80. More specifically, as shown in the example of FIG. 4, a convolution 404 (e.g., a 5×5 convolution, etc.) is applied to a portion or window (also referred to as a "receptive field") 402 of the input 310 (e.g., a 32×32 data input, etc.) in the first layer 320 to provide a feature map 406 (e.g., a (6×) 28×28 feature map, etc.). The convolution 404 maps the elements from the input 310 to the feature map 406. The first layer 320 also provides subsampling (e.g., 2×2 subsampling, etc.) to generate a reduced feature map 410 (e.g., a (6×) 14×14 feature map, etc). The feature map 410 undergoes a convolution 412 and is propagated from the first layer 320 to the second layer 340, where the feature map 410 becomes an expanded feature map 414 (e.g., a (16×) 10×10 feature map, etc.). After subsampling 416 in the second layer 340, the feature map 414 becomes a reduced feature map 418 (e.g., a (16×) 4×5 feature map, etc.). The feature map 418 undergoes a convolution 420 and is propagated to the third layer 360, where the feature map 418 becomes a classification layer 422 forming an output layer of N categories 424 with connection 426 to the convoluted layer 422, for example.

Figure 5:
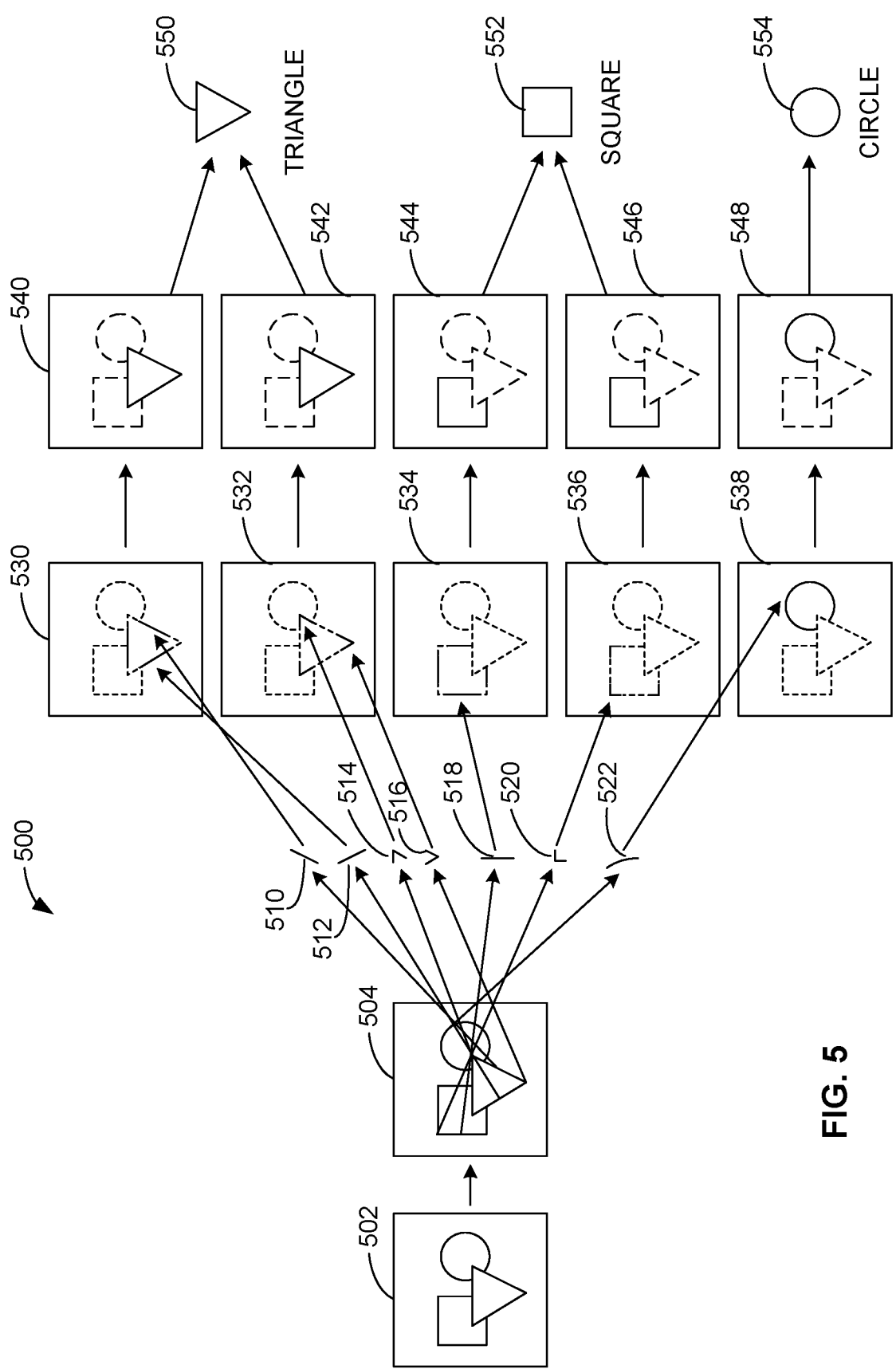
FIG. 5 is a representation of an example implementation of an image analysis convolutional neural network.

FIG. 5 is a representation of an example implementation of an image analysis convolutional neural network 500. The convolutional neural network 500 receives an input image 502 and abstracts the image in a convolution layer 504 to identify learned features 510-522. In a second convolution layer 530, the image is transformed into a plurality of images 530-538 in which the learned features 510-522 are each accentuated in a respective sub-image 530-538. The images 530-538 are further processed to focus on the features of interest 510-522 in images 540-548. The resulting images 540-548 are then processed through a pooling layer which reduces the size of the images 540-548 to isolate portions 550-554 of the images 540-548 including the features of interest 510-522. Outputs 550-554 of the convolutional neural network 500 receive values from the last non-output layer and classify the image based on the data received from the last non-output layer. In certain examples, the convolutional neural network 500 may contain many different variations of convolution layers, pooling layers, learned features, and outputs, etc.

Figure 6A:
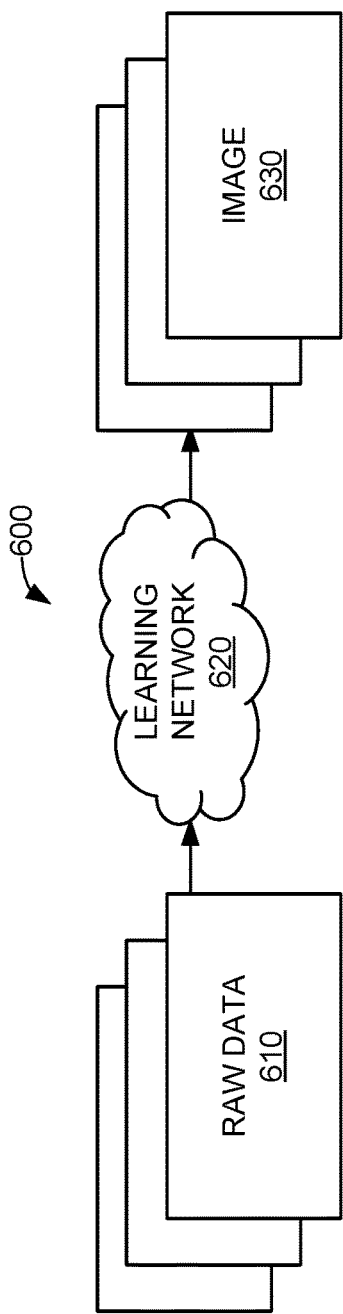
FIG. 6A illustrates an example configuration to apply a learning network to process and/or otherwise evaluate an image.

FIG. 6A illustrates an example configuration 600 to apply a learning (e.g., machine learning, deep learning, etc.) network to process and/or otherwise evaluate an image. Machine learning can be applied to a variety of processes including image acquisition, image reconstruction, image analysis/diagnosis, etc. As shown in the example configuration 600 of FIG. 6A, raw data 610 (e.g., raw data 610 such as sonogram raw data, etc., obtained from an imaging scanner such as an x-ray, computed tomography, ultrasound, magnetic resonance, etc., scanner) is fed into a learning network 620. The learning network 620 processes the data 610 to correlate and/or otherwise combine the raw image data 620 into a resulting image 630 (e.g., a "good quality" image and/or other image providing sufficient quality for diagnosis, etc.). The learning network 620 includes nodes and connections (e.g., pathways) to associate raw data 610 with a finished image 630. The learning network 620 can be a training network that learns the connections and processes feedback to establish connections and identify patterns, for example. The learning network 620 can be a deployed network that is generated from a training network and leverages the connections and patterns established in the training network to take the input raw data 610 and generate the resulting image 630, for example.

Once the learning 620 is trained and produces good images 630 from the raw image data 610, the network 620 can continue the "self-learning" process and refine its performance as it operates. For example, there is "redundancy" in the input data (raw data) 610 and redundancy in the network 620, and the redundancy can be exploited.

If weights assigned to nodes in the learning network 620 are examined, there are likely many connections and nodes with very low weights. The low weights indicate that these connections and nodes contribute little to the overall performance of the learning network 620. Thus, these connections and nodes are redundant. Such redundancy can be evaluated to reduce redundancy in the inputs (raw data) 610. Reducing input 610 redundancy can result in savings in scanner hardware, reduced demands on components, and also reduced exposure dose to the patient, for example.

In deployment, the configuration 600 forms a package 600 including an input definition 610, a trained network 620, and an output definition 630. The package 600 can be deployed and installed with respect to another system, such as an imaging system, analysis engine, etc.

Figure 6B:
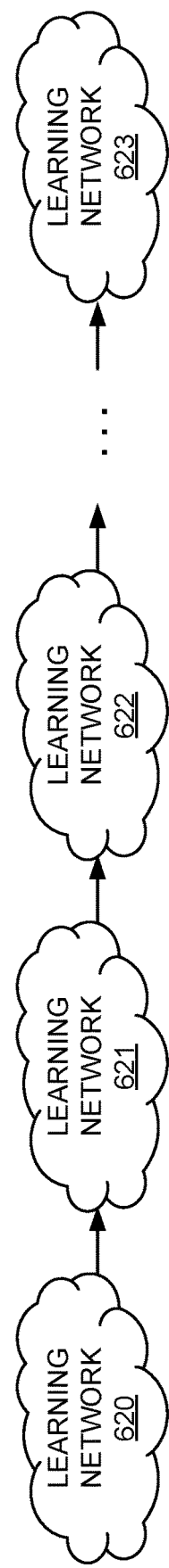
FIG. 6B illustrates a combination of a plurality of learning networks.

As shown in the example of FIG. 6B, the learning network 620 can be chained and/or otherwise combined with a plurality of learning networks 621-623 to form a larger learning network. The combination of networks 620-623 can be used to further refine responses to inputs and/or allocate networks 620-623 to various aspects of a system, for example.

In some examples, in operation, "weak" connections and nodes can initially be set to zero. The learning network 620 then processes its nodes in a retaining process. In certain examples, the nodes and connections that were set to zero are not allowed to change during the retraining. Given the redundancy present in the network 620, it is highly likely that equally good images will be generated. As illustrated in FIG. 6B, after retraining, the learning network 620 becomes DLN 621. The learning network 621 is also examined to identify weak connections and nodes and set them to zero. This further retrained network is learning network 622. The example learning network 622 includes the "zeros" in learning network 621 and the new set of nodes and connections. The learning network 622 continues to repeat the processing until a good image quality is reached at a learning network 623, which is referred to as a "minimum viable net (MVN)". The learning network 623 is a MVN because if additional connections or nodes are attempted to be set to zero in learning network 623, image quality can suffer.

Once the MVN has been obtained with the learning network 623, "zero" regions (e.g., dark irregular regions in a graph) are mapped to the input 610. Each dark zone is likely to map to one or a set of parameters in the input space. For example, one of the zero regions may be linked to the number of views and number of channels in the raw data. Since redundancy in the network 623 corresponding to these parameters can be reduced, there is a highly likelihood that the input data can be reduced and generate equally good output. To reduce input data, new sets of raw data that correspond to the reduced parameters are obtained and run through the learning network 621. The network 620-623 may or may not be simplified, but one or more of the learning networks 620-623 is processed until a "minimum viable input (MVI)" of raw data input 610 is reached. At the MVI, a further reduction in the input raw data 610 may result in reduced image 630 quality. The MVI can result in reduced complexity in data acquisition, less demand on system components, reduced stress on patients (e.g., less breath-hold or contrast), and/or reduced dose to patients, for example.

By forcing some of the connections and nodes in the learning networks 620-623 to zero, the network 620-623 to build "collaterals" to compensate. In the process, insight into the topology of the learning network 620-623 is obtained. Note that network 621 and network 622, for example, have different topology since some nodes and/or connections have been forced to zero. This process of effectively removing connections and nodes from the network extends beyond "deep learning" and can be referred to as "deep-deep learning", for example.

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 7:
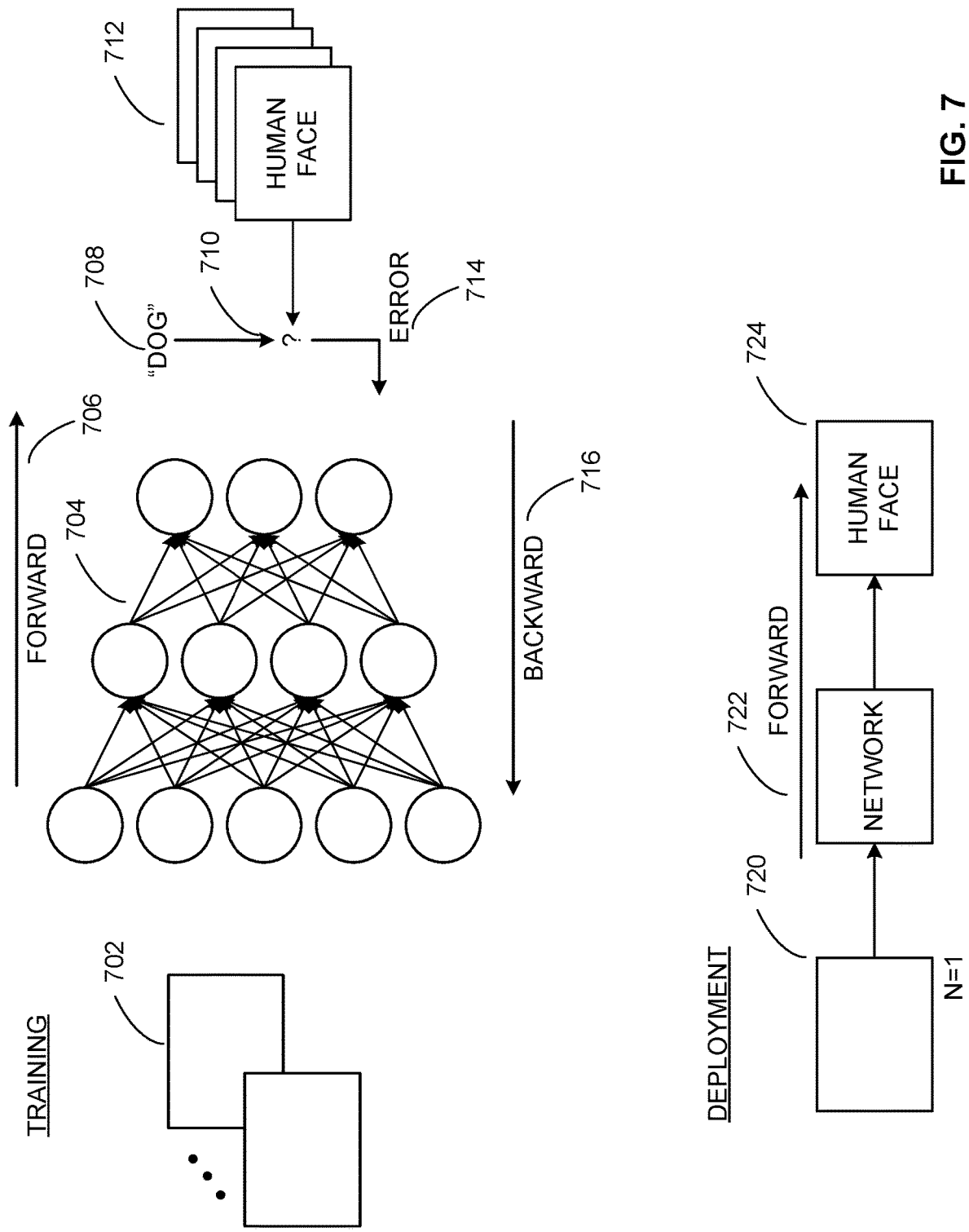
FIG. 7 illustrates example training and deployment phases of a learning network.

FIG. 7 illustrates example training and deployment phases of a learning network, such as a deep learning or other machine learning network. As shown in the example of FIG. 7, in the training phase, a set of inputs 702 is provided to a network 704 for processing. In this example, the set of inputs 702 can include facial features of an image to be identified. The network 704 processes the input 702 in a forward direction 706 to associate data elements and identify patterns. The network 704 determines that the input 702 represents a dog 708. In training, the network result 708 is compared 710 to a known outcome 712. In this example, the known outcome 712 is a human face (e.g., the input data set 702 represents a human face, not a dog face). Since the determination 708 of the network 704 does not match 710 the known outcome 712, an error 714 is generated. The error 714 triggers an analysis of the known outcome 712 and associated data 702 in reverse along a backward pass 716 through the network 704. Thus, the training network 704 learns from forward 706 and backward 716 passes with data 702, 712 through the network 704.

Once the comparison of network output 708 to known output 712 matches 710 according to a certain criterion or threshold (e.g., matches n times, matches greater than x percent, etc.), the training network 704 can be used to generate a network for deployment with an external system. Once deployed, a single input 720 is provided to a deployed learning network 722 to generate an output 724. In this case, based on the training network 704, the deployed network 722 determines that the input 720 is an image of a human face 724.

Figure 8:
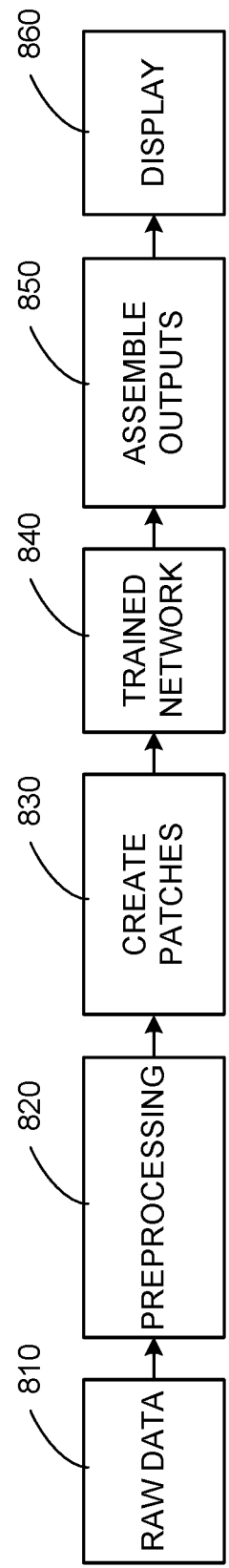
FIG. 8 illustrates an example product leveraging a trained network package to provide a deep learning product offering.

FIG. 8 illustrates an example product leveraging a trained network package to provide a deep and/or other machine learning product offering. As shown in the example of FIG. 8, an input 810 (e.g., raw data) is provided for preprocessing 820. For example, the raw input data 810 is preprocessed 820 to check format, completeness, etc. Once the data 810 has been preprocessed 820, patches are created 830 of the data. For example, patches or portions or "chunks" of data are created 830 with a certain size and format for processing. The patches are then fed into a trained network 840 for processing. Based on learned patterns, nodes, and connections, the trained network 840 determines outputs based on the input patches. The outputs are assembled 850 (e.g., combined and/or otherwise grouped together to generate a usable output, etc.). The output is then displayed 860 and/or otherwise output to a user (e.g., a human user, a clinical system, an imaging modality, a data storage (e.g., cloud storage, local storage, edge device, etc.), etc.).

Figure 9A:
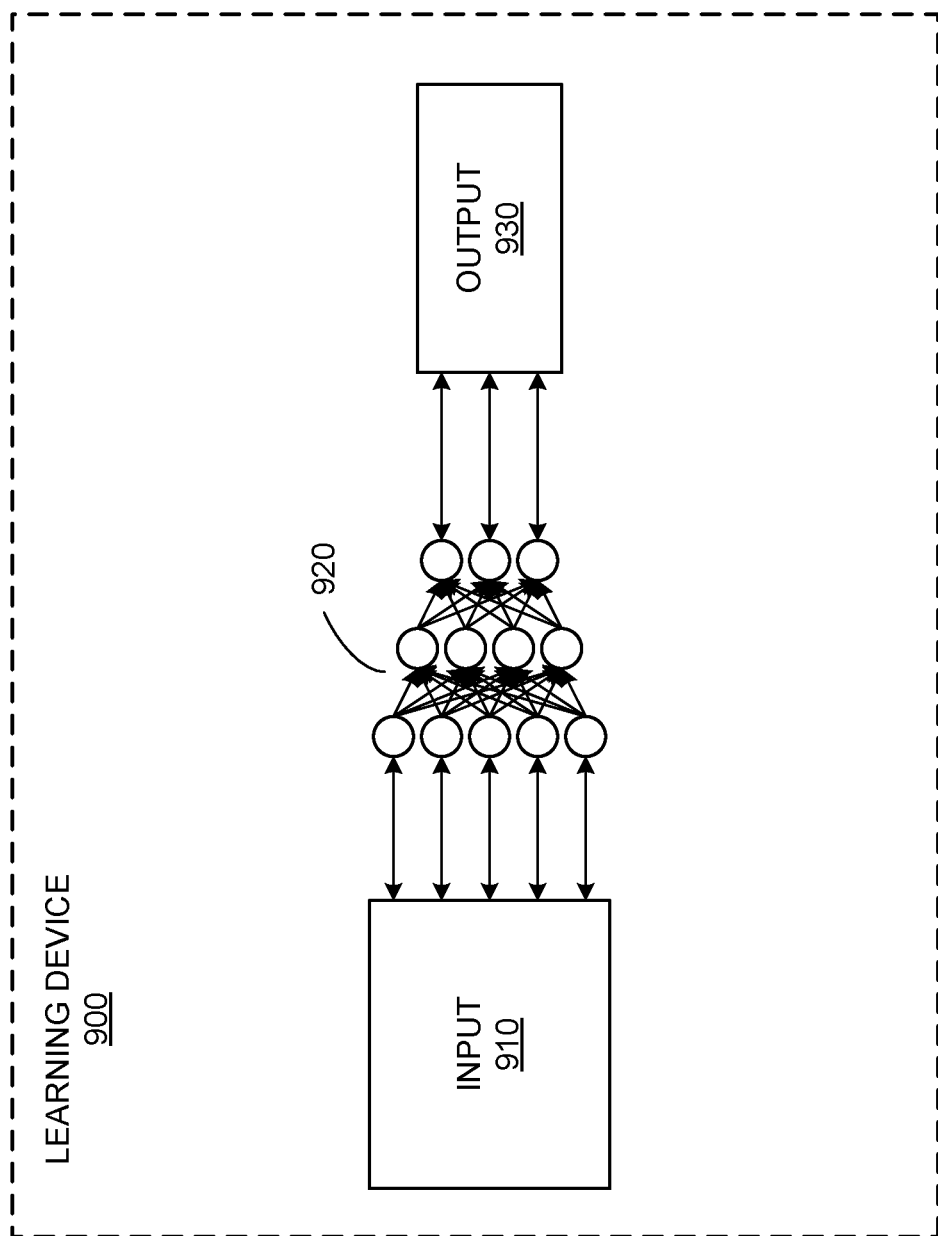
FIGS. 9A-9C illustrate various deep learning device configurations.
Figure 9B:
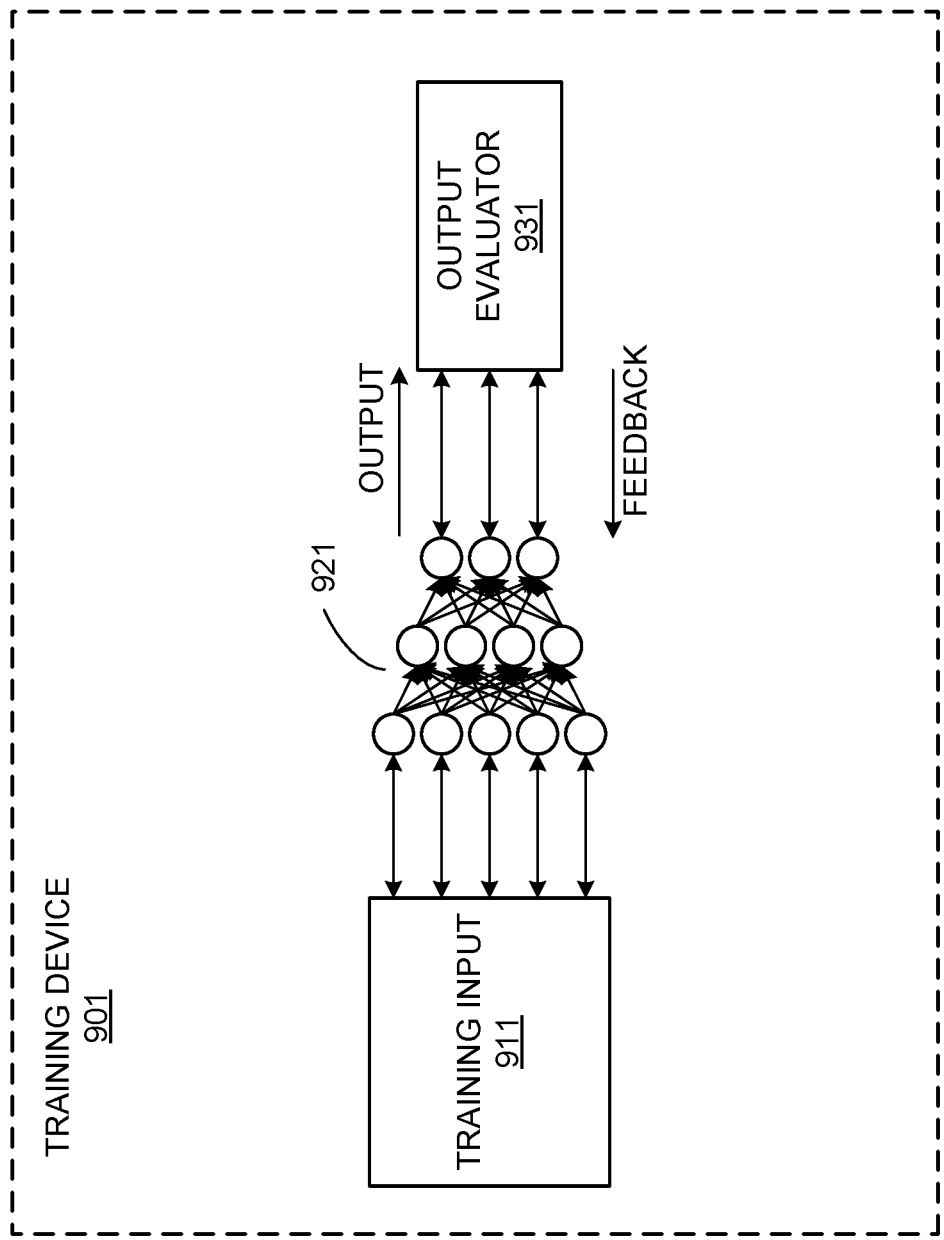
Figure 9C:
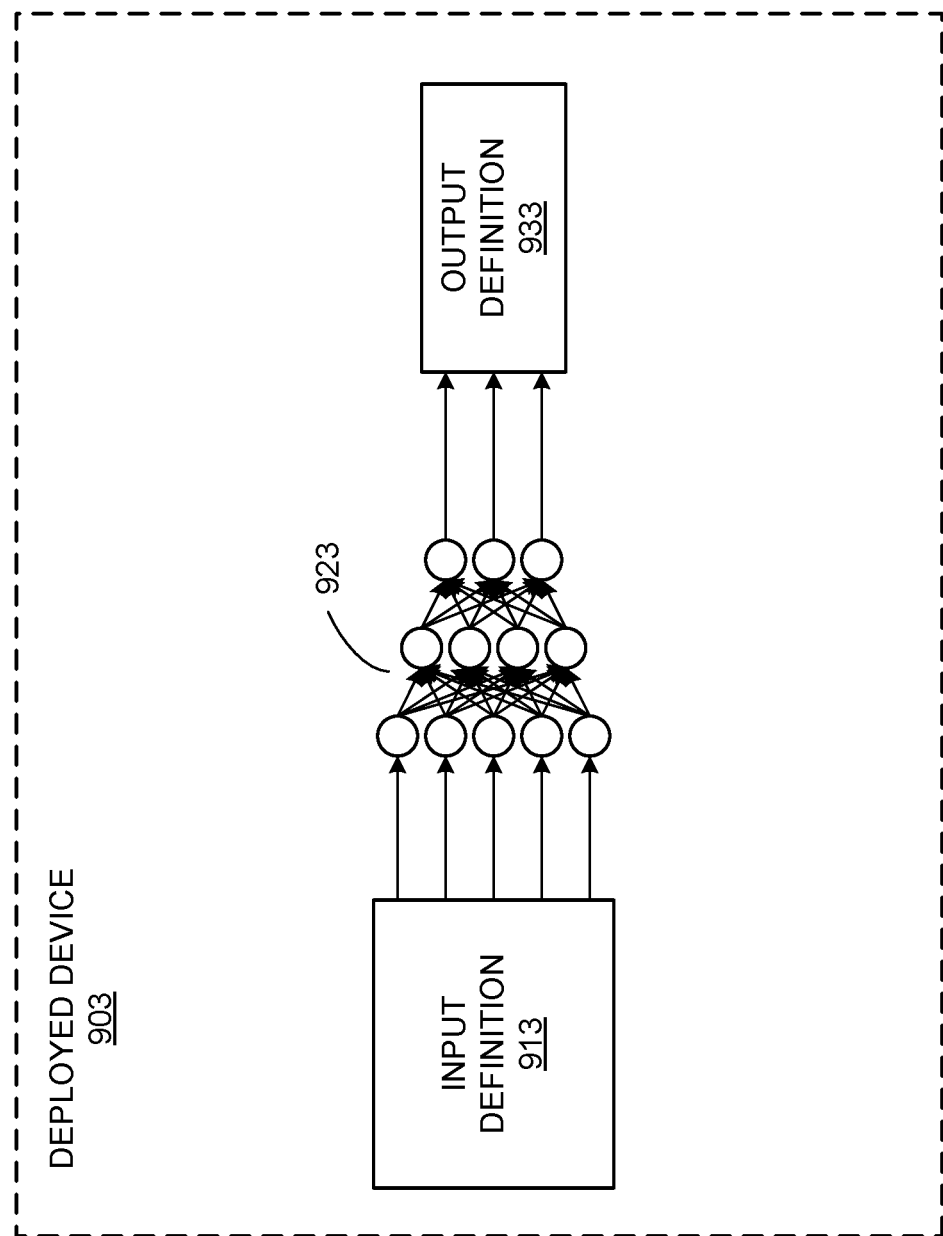

As discussed above, learning networks can be packaged as devices for training, deployment, and application to a variety of systems. FIGS. 9A-9C illustrate various learning device configurations. For example, FIG. 9A shows a general learning device 900. The example device 900 includes an input definition 910, a learning network model 920, and output definitions 930. The input definition 910 can include one or more inputs translating into one or more outputs 930 via the network 920.

FIG. 9B shows an example training device 901. That is, the training device 901 is an example of the device 900 configured as a training learning network device. In the example of FIG. 9B, a plurality of training inputs 911 are provided to a network 921 to develop connections in the network 921 and provide an output to be evaluated by an output evaluator 931. Feedback is then provided by the output evaluator 931 into the network 921 to further develop (e.g., train) the network 921. Additional input 911 can be provided to the network 921 until the output evaluator 931 determines that the network 921 is trained (e.g., the output has satisfied a known correlation of input to output according to a certain threshold, margin of error, etc.).

FIG. 9C depicts an example deployed device 903. Once the training device 901 has learned to a requisite level, the training device 901 can be deployed for use. While the training device 901 processes multiple inputs to learn, the deployed device 903 processes a single input to determine an output, for example. As shown in the example of FIG. 9C, the deployed device 903 includes an input definition 913, a trained network 923, and an output definition 933. The trained network 923 can be generated from the network 921 once the network 921 has been sufficiently trained, for example. The deployed device 903 receives a system input 913 and processes the input 913 via the network 923 to generate an output 933, which can then be used by a system with which the deployed device 903 has been associated, for example.

Example Image Analysis and Prostate Evaluation Systems and Methods

Certain examples provide systems and methods for computer-assisted diagnostics and classification of prostate cancer. For example, certain examples position a prostate lesion on a prostate sector map using multimodal multi-protocol MR data and integrate prostate lesion information for a computer-aided diagnosis and classification system for prostate cancer.

For example, in a first workflow, a graphical object (e.g., ROI/long axis) is deposited on a lesion in one or more acquired images. Additionally, an ellipse is deposited on a prostate sector map, with schema and sector(s) underneath the map automatically selected. The lesion can then be scored according to PIRADS v2 guidelines. Based on the lesion mapping and score, a report and/or next action trigger can be generated and exported.

In another workflow, for example, MR image acquisition is performed, and resulting image(s) are loaded and displayed. Patient clinical history is obtained (e.g., from a clinician, patient, electronic medical record, etc.), and the patient's PSA level is determined. The prostate is automatically segmented and its volume is computed (e.g., using deep learning-based methods, etc.). A graphical object (e.g., ROI/long axis) is deposited on the MR data, and corresponding sector(s) is(are) automatically selected (e.g., using non-rigid registration of the segmented prostate and a three-dimensional (3D) model of the prostate sector map, etc.). Lesion(s) can then be scored according to PIRADS v2 guidelines. Based on the region analysis and lesion score, a report and/or next action trigger can be generated and exported.

In another workflow, for example, MR image acquisition is performed, and resulting image(s) are loaded and displayed. Patient clinical history is obtained (e.g., from a clinician, patient, electronic medical record, etc.), and the patient's PSA level is determined. The prostate is automatically segmented and its volume is computed (e.g., using deep learning-based methods, etc.). Lesion(s) are automatically segmented and then located and scored for each available MR imaging technique (e.g., using non-rigid registration of the segmented prostate and a 3D model of the prostate sector map and deep learning based methods, etc.). Based on the lesion segmentation, analysis and score, a report and/or next action trigger can be generated and exported.

In certain examples, a deep learning network model can process the image data to generate a binary mask output to identify a lesion on the prostate gland in the image(s). The model can take one or more image slices, a three-dimensional volume, etc. (e.g., that has been pre-processed to normalize intensity and/or resolution, etc.), and segment the image data via the network to provide a binary mask identifying the lesion in the image data. The lesion can be positioned on a prostate sector map using multimodal multi-protocol MR data via the network model, for example.

Thus, certain examples provide processing, review, analysis, and communication of 3D reconstructed images and their relationship to originally acquired images from MR scanning devices. A combination of acquired images, reconstructed images, annotations, and measurements performed by the clinician and/or automatically using deep learning and/or other artificial intelligence provide a referring physician with clinically relevant information that can aid in diagnosis and treatment planning, for example.

Figure 10:
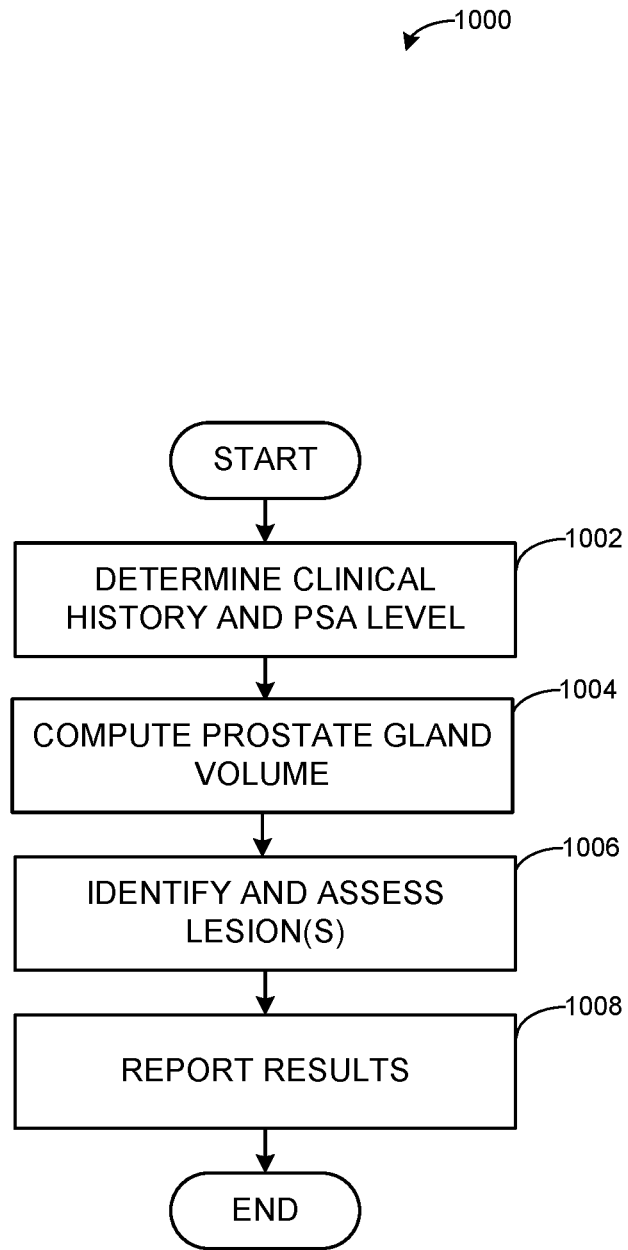
FIG. 10 illustrates a flow diagram of an example method for computer-driven prostate analysis.
Figure 11:
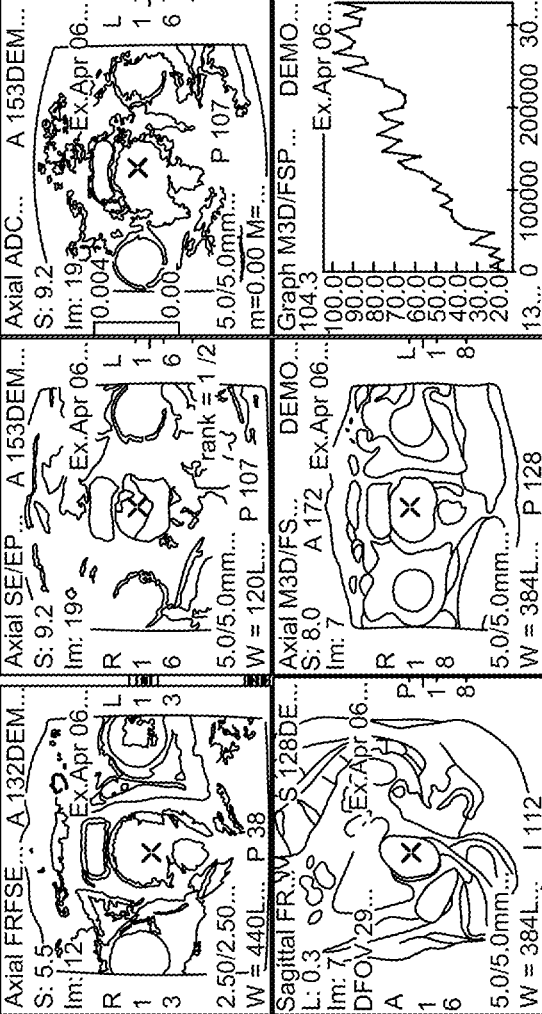
Figure 12:
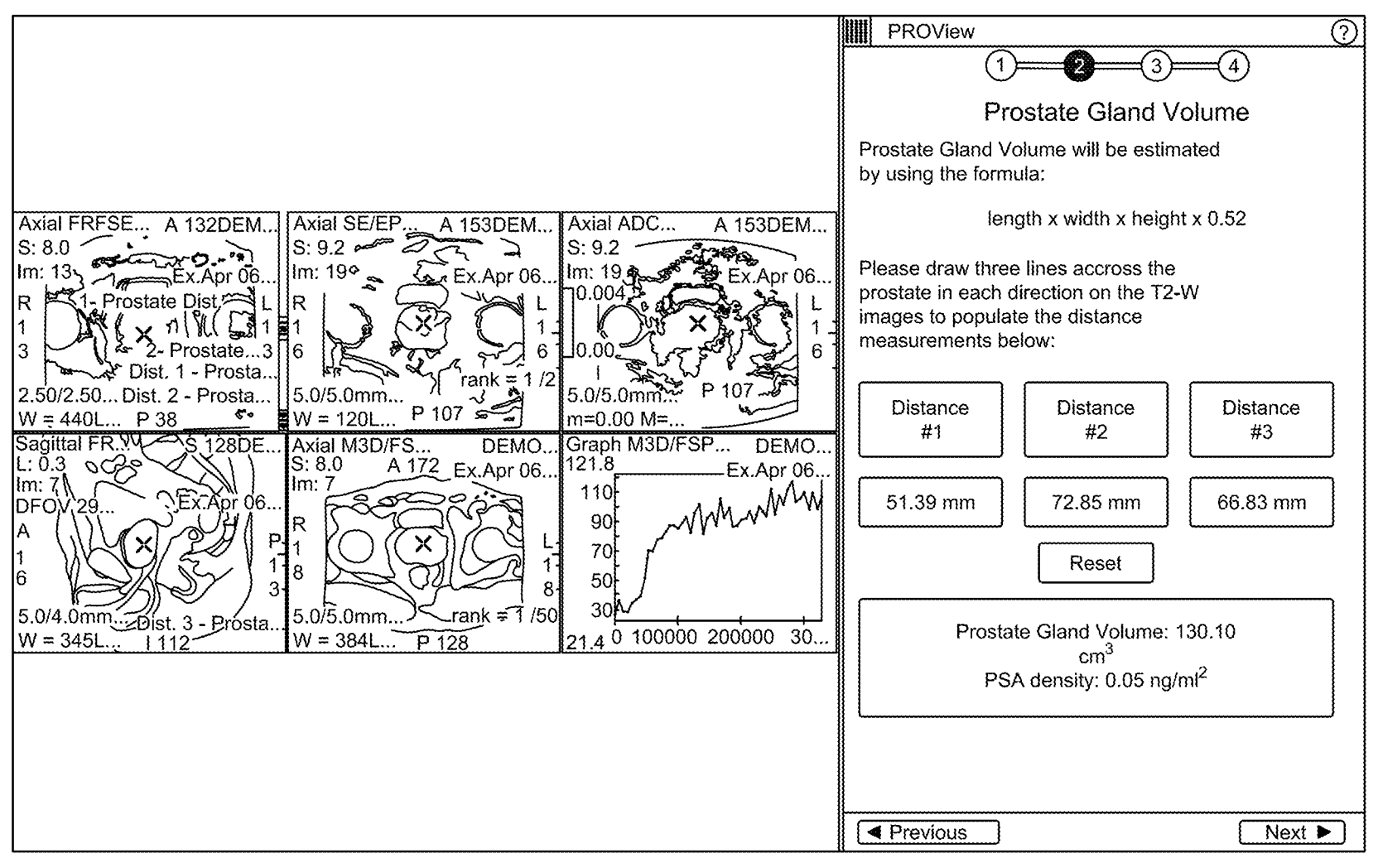

FIG. 10 illustrates an example method and associated infrastructure to analyze prostate information and generate a prediction and/or other analysis regarding likely prostate cancer, malignant lesion, and/or other prostate issue. At block 1002, patient clinical history and PSA level are determined (see, e.g., the example interface of FIG. 11). At block 1004, prostate gland volume is computed. For example, distances (e.g., 3 distances, etc.) are deposited on the image (e.g., using a dedicated distance tool, etc.) and prostate volume and PSA density are computed automatically (see, e.g., the example interface of FIG. 12). For example, the prostate volume can be automatically computed using three distances drawn on the prostate in the image via the user interface to mark the length (d1), width (d2), and height (d3) of the prostate gland in the image. The prostate gland volume can then be computed as length×width×height×0.52=prostate gland volume, where 0.52 is an example of a scaling factor to account for differences between actual size and representation in the image data. PSA density can then be computed from the prostate gland volume and other factors, for example.

Figure 13:
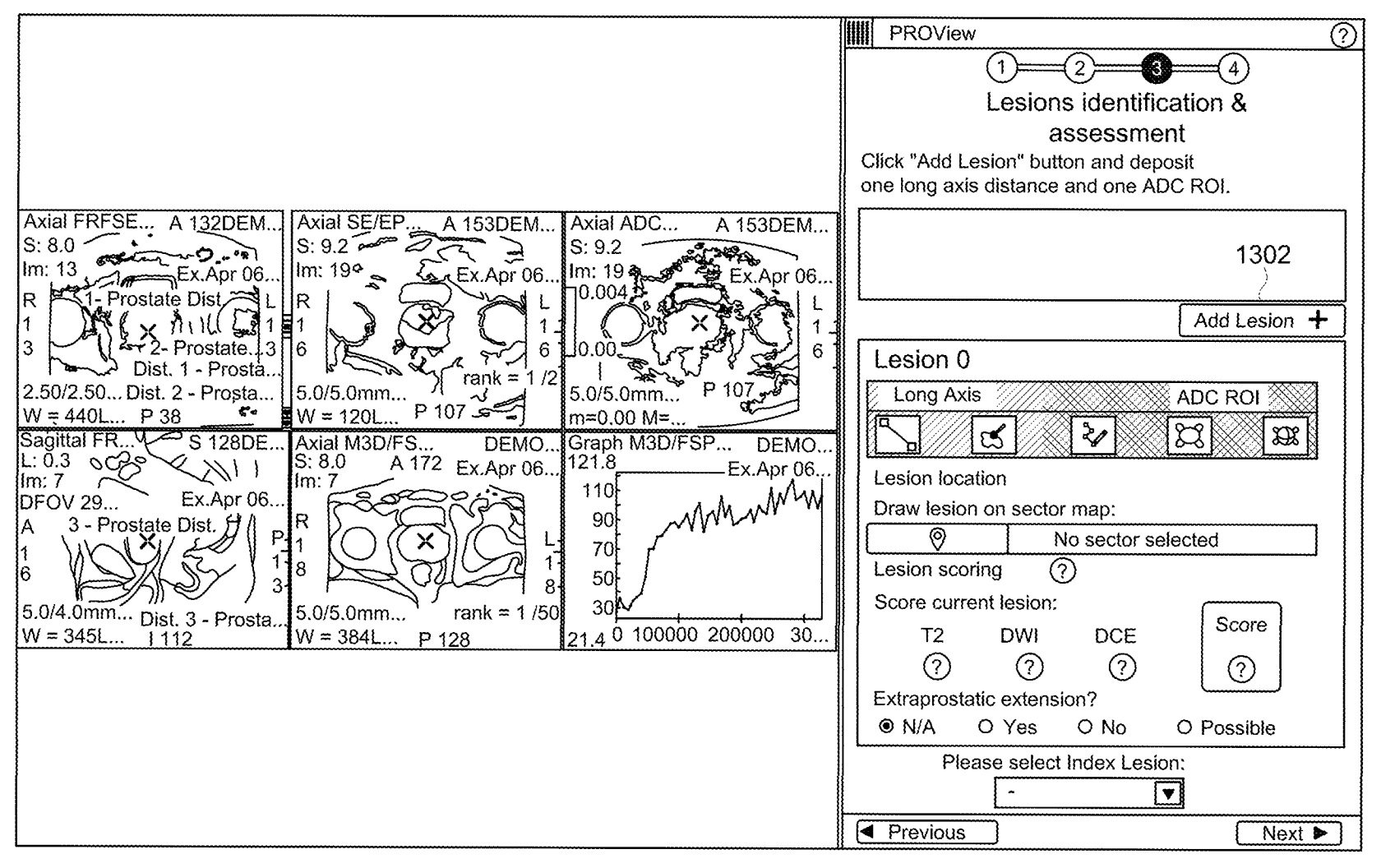
Figure 14:
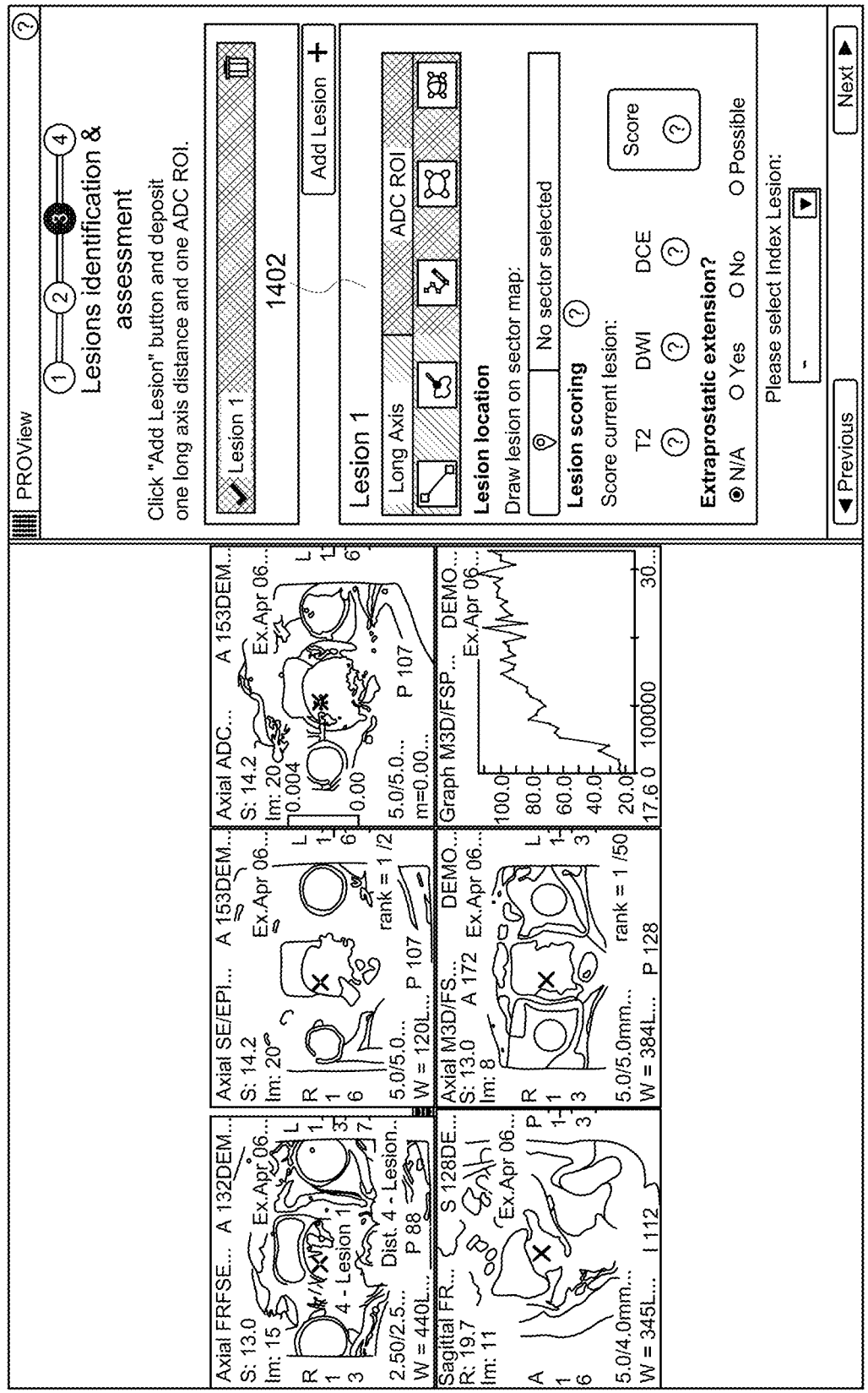
Figure 15:
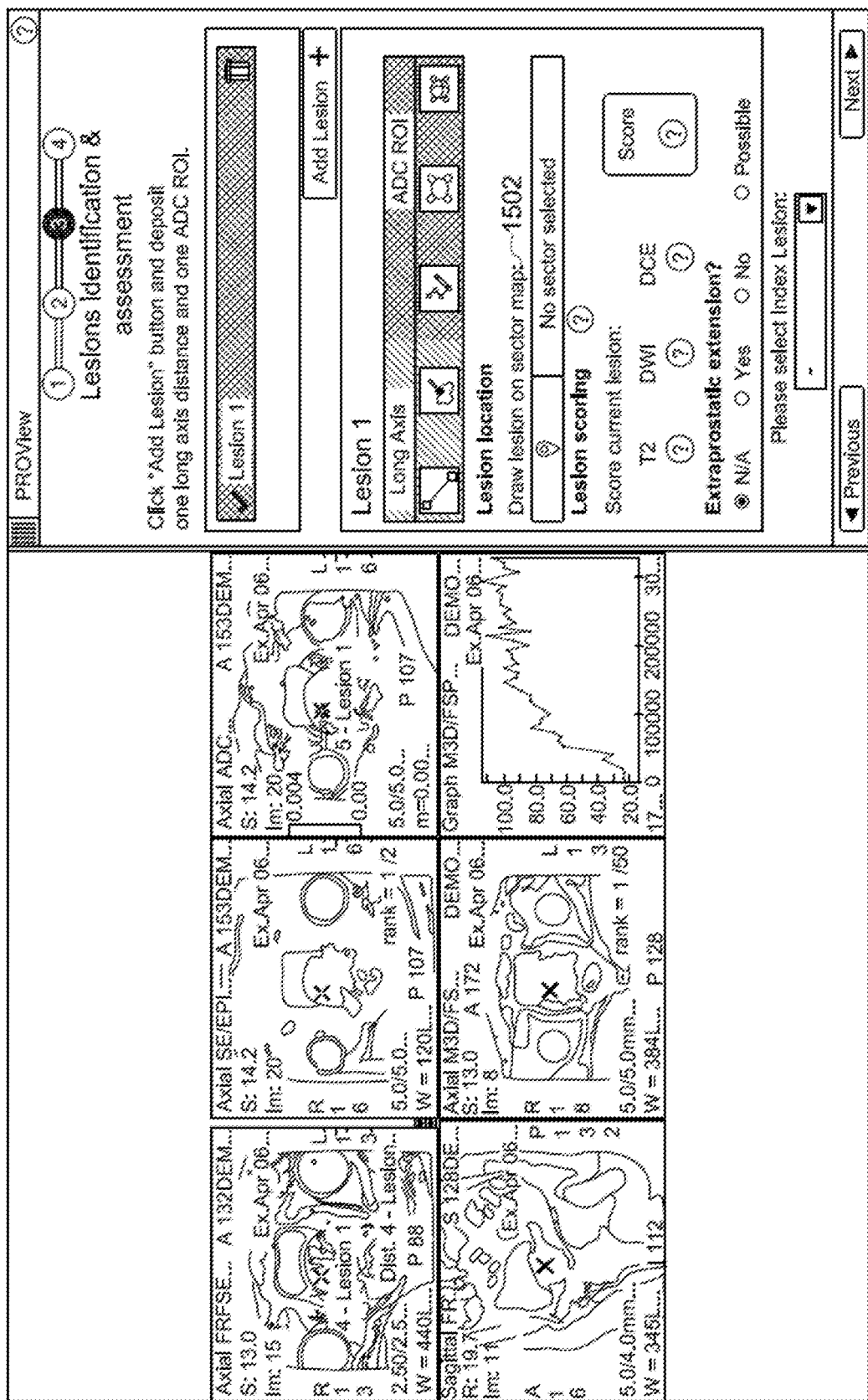
Figure 16:
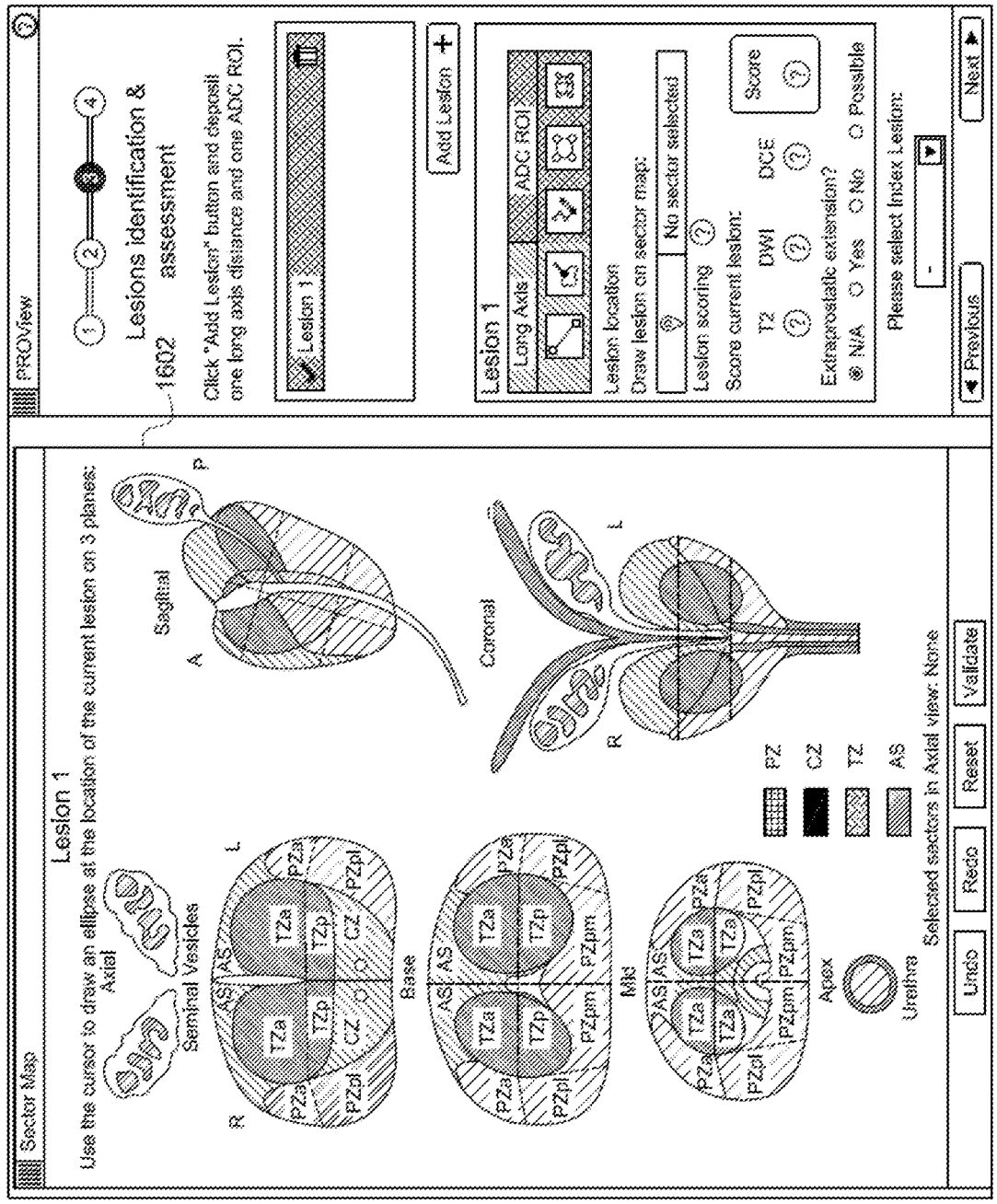
Figure 17:
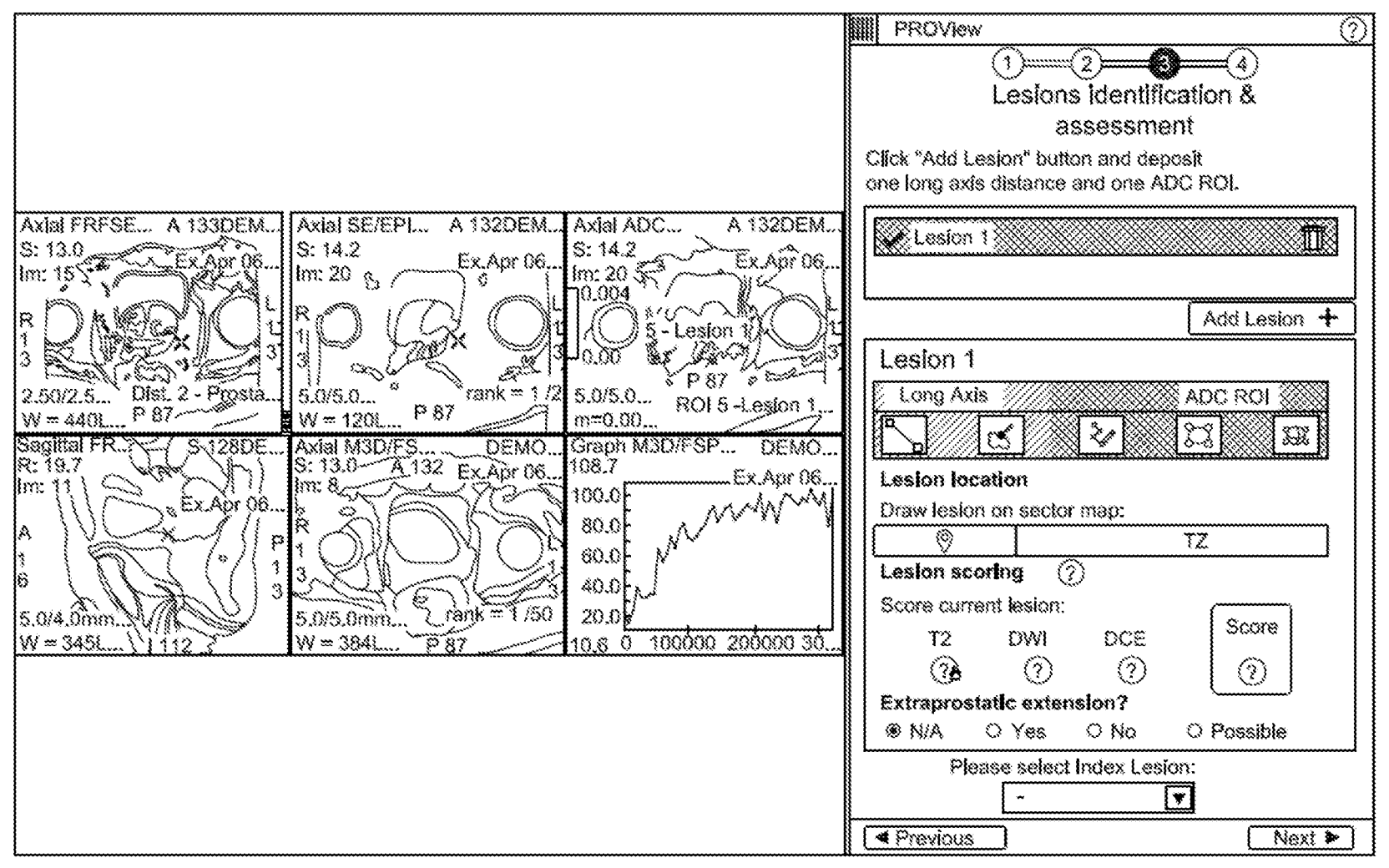

At block 1006, lesion(s) are identified and assessed. Lesion(s) can be identified and analyzed in a plurality of implementations. For example, a new lesion can be added (e.g., labeled) on MR image(s) (see, e.g., at 1302 in the example interface of FIG. 13). For example, a long axis distance and an ADC region of interest (ROI) can be deposited on the image(s) via the interface. As another example, lesion(s) are identified using available tools, algorithms, digital twin, etc. (see, e.g., 1402 in the example interface of FIG. 14). Another example of lesion location determination 1502 is shown in the example graphical user interface of FIG. 15. As shown in the example interface of FIG. 16, ellipses are deposited on axial, sagittal, and coronal planes in the interface 1602 to automatically select corresponding sectors. For example, once an ellipse is positioned on a prostate sector map schema, sector(s) underneath the ellipse are automatically selected. In FIG. 17, lesions are scored on each available MR technique, and a global score is automatically computed from the MR technique lesion scores, for example. For example, a lesion score can be based on its size (e.g., length, width, volume, etc.), position, etc., and scores can include a T1-weighted pulse sequence score, a T2-weighted pulse sequence score, a diffusion-weighted imaging (DWI) score, a dynamic contrast-enhanced (DCE) MRI score, an overall score, etc.

Figure 18:
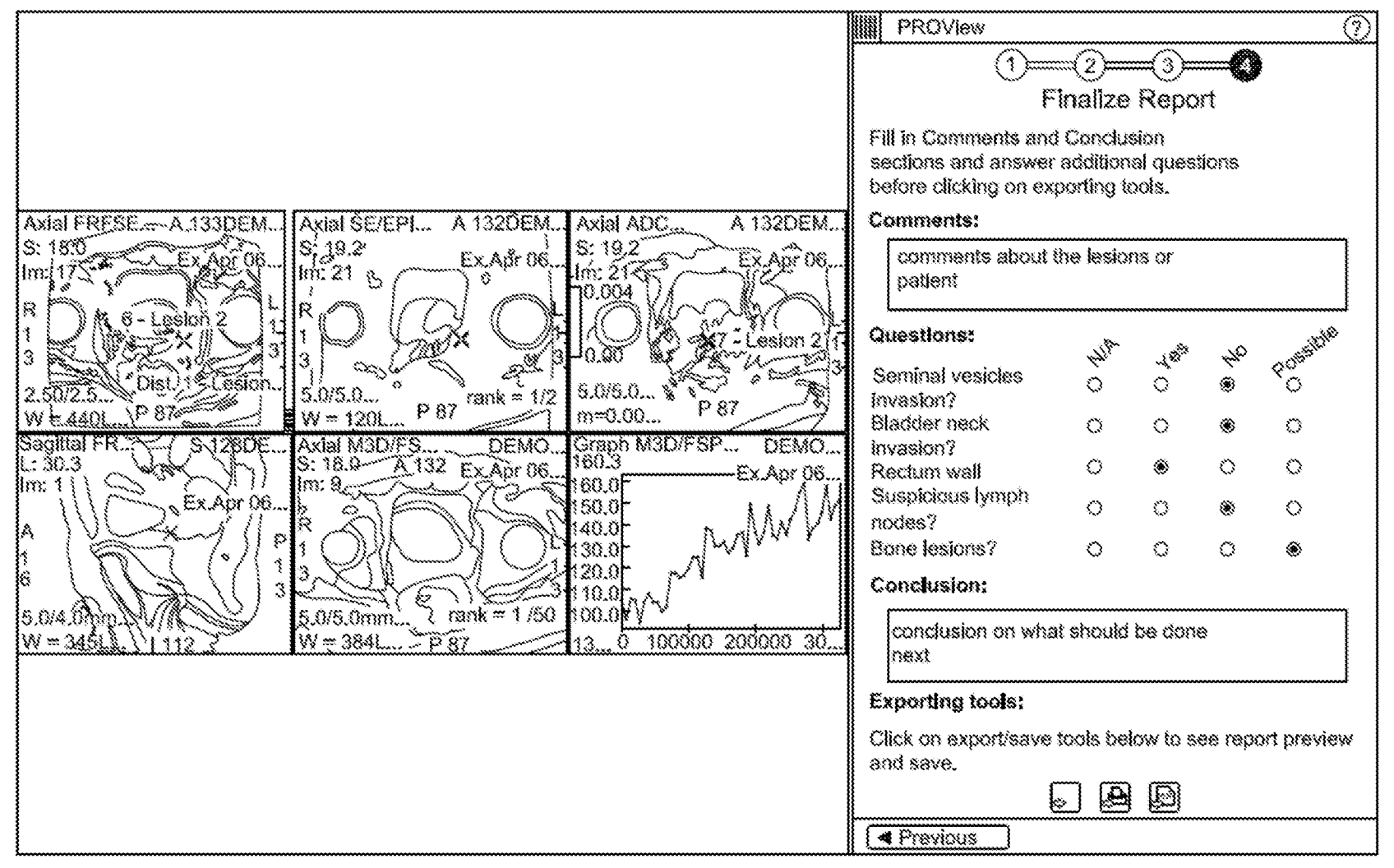

At block 1008, a report can be generated, saved, output, transferred, etc. (see, e.g., the example interface of FIG. 18).

Figure 19B:
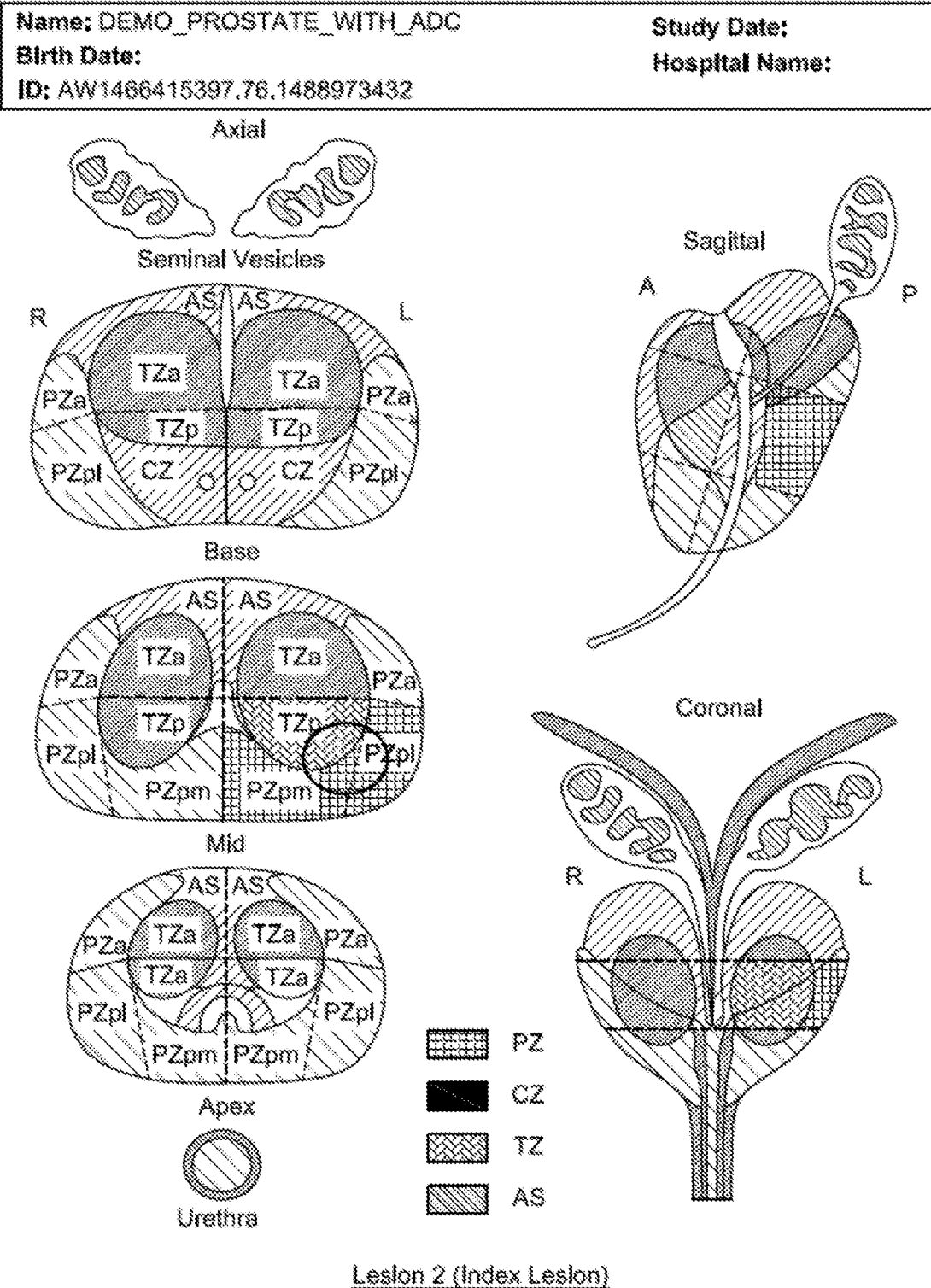
Figure 19C:
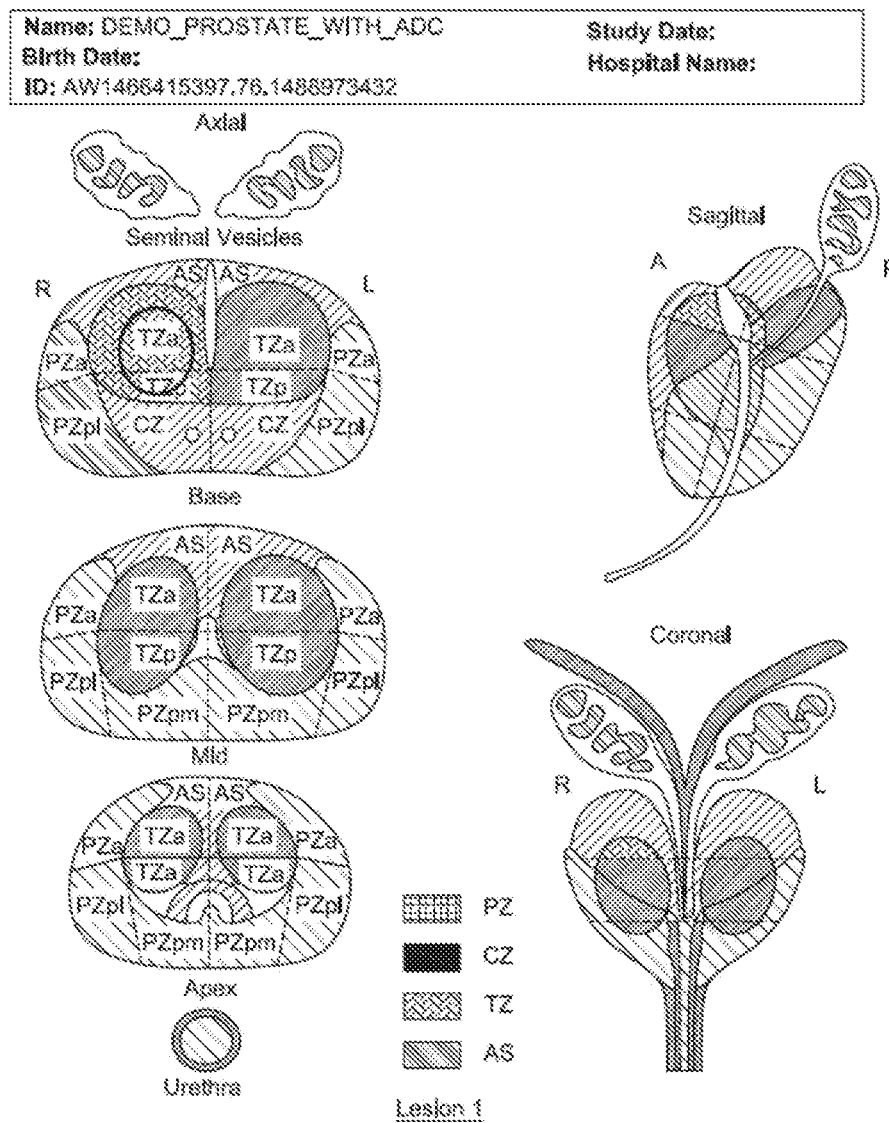

FIGS. 19A-19C illustrate an example report showing prostate evaluation, score, PI-RADS assessment, ADC information, etc. For example, patient clinical history (e.g., including an identified trend in PSA level, etc.), prostate gland volume, PSA level, PSA density, lesion details, index lesion, comments, PI-RADS assessment, conclusion, etc., can be provided (e.g., transmitted to another program, trigger another process, saved, displayed, and/or otherwise output) based on the analysis to drive further action with respect to the patient.

Thus, axial and sagittal MR image views can be used in a training set as well as an evaluation set to develop and test a deep learning network, such as the network 300, 400, 500, to analyze MR prostate image data and identify and classify lesion(s) in the image. From the lesion information, a conclusion, recommendation, and/or other evaluation regarding likely prostate issue(s) can be determined. Qualitative evaluation, hidden layer processing in a deep neural network, and an analysis of edges, edge combination(s), object models, etc enable the deep neural network to correlate MR image data with likely prostate lesions and/or other imperfections necessitating follow-up for further verification, treatment, etc. Convolution, deconvolution, forward inference and backward learning from image segmentation and pixel intensity data can help drive a correlation between MR image information and likely prostate cancer determination via CAD, for example.

While example implementations are illustrated in conjunction with FIGS. 1-19C, elements, processes and/or devices illustrated in conjunction with FIGS. 1-19C may be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts representative of example machine readable instructions for implementing components disclosed and described herein are shown in conjunction with at least FIG. 10. In the examples, the machine readable instructions include a program for execution by a processor such as the processor 2012 shown in the example processor platform 2000 discussed below in connection with FIG. 20. The program may be embodied in machine readable instructions stored on a tangible computer readable storage medium such as a CD-ROM, a floppy disk, a hard drive, a digital versatile disk (DVD), a Blu-ray disk, or a memory associated with the processor 2012, but the entire program and/or parts thereof could alternatively be executed by a device other than the processor 2012 and/or embodied in firmware or dedicated hardware. Further, although the example program is described with reference to the flowcharts illustrated in conjunction with at least FIG. 10, many other methods of implementing the components disclosed and described herein may alternatively be used. For example, the order of execution of the blocks may be changed, and/or some of the blocks described may be changed, eliminated, or combined. Although the flowcharts of at least FIG. 10 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIG. 10 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIG. 10 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 20:
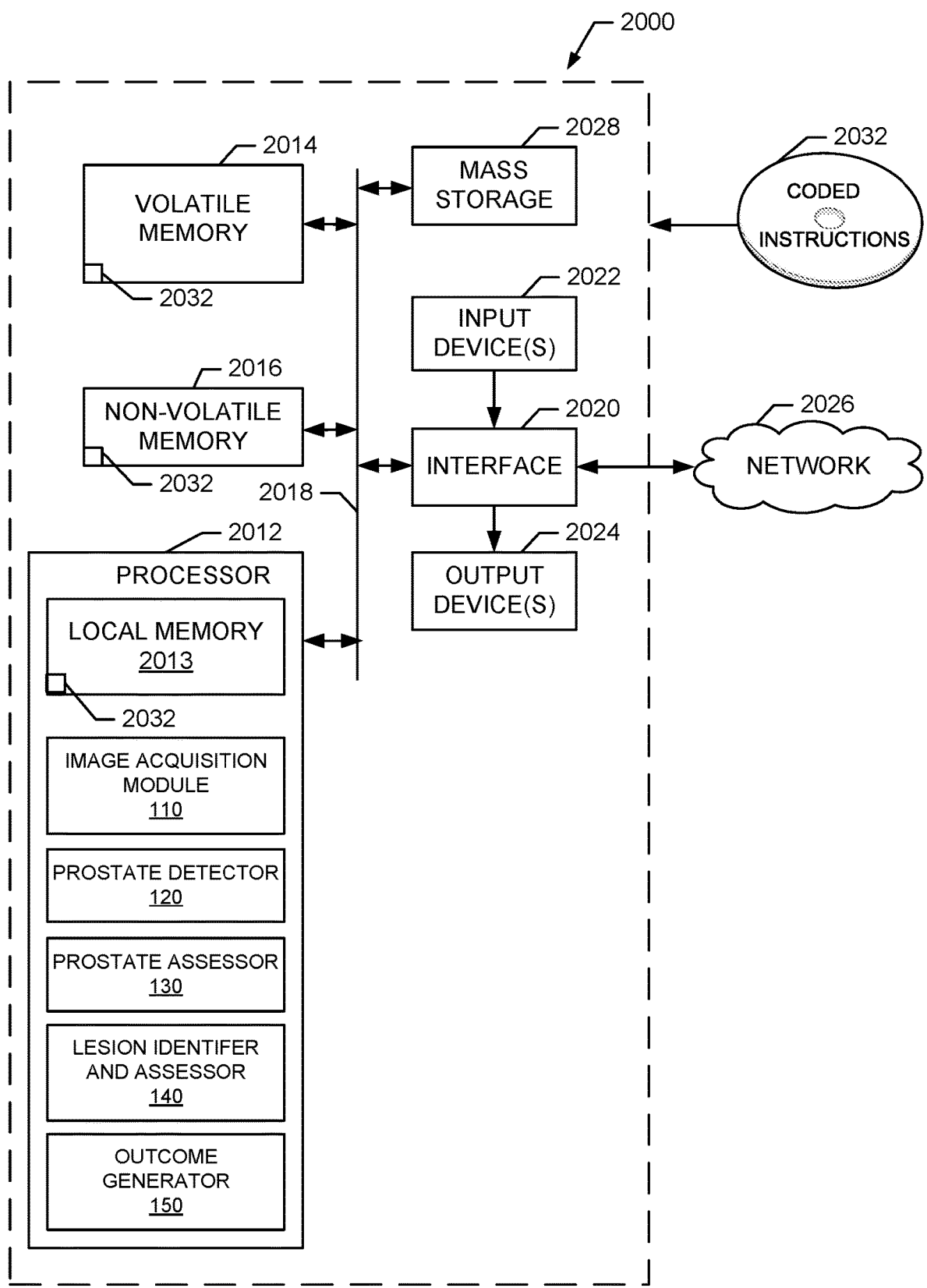
FIG. 20 is a block diagram of a processor platform structured to execute the example machine readable instructions to implement components disclosed and described herein.

FIG. 20 is a block diagram of an example processor platform 2000 structured to executing the instructions of at least FIG. 10 to implement the example components disclosed and described herein. The processor platform 2000 can be, for example, a server, a personal computer, a mobile device (e.g., a cell phone, a smart phone, a tablet such as an iPad™), a personal digital assistant (PDA), an Internet appliance, or any other type of computing device.

The processor platform 2000 of the illustrated example includes a processor 2012. The processor 2012 of the illustrated example is hardware. For example, the processor 2012 can be implemented by integrated circuits, logic circuits, microprocessors or controllers from any desired family or manufacturer.

The processor 2012 of the illustrated example includes a local memory 2013 (e.g., a cache). The example processor 2012 of FIG. 20 executes the instructions of at least FIG. 10 to implement the systems and infrastructure and associated methods of FIGS. 1-19C such as an image acquisition module, a prostate detector, a prostate assessor, a lesion identifier and assessor, an outcome generator, etc. The processor 2012 of the illustrated example is in communication with a main memory including a volatile memory 2014 and a non-volatile memory 2016 via a bus 2018. The volatile memory 2014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2016 may be implemented by flash memory and/or any other desired type of memory device. Access to the main memory 2014, 2016 is controlled by a clock controller.

The processor platform 2000 of the illustrated example also includes an interface circuit 2020. The interface circuit 2020 may be implemented by any type of interface standard, such as an Ethernet interface, a universal serial bus (USB), and/or a PCI express interface.

In the illustrated example, one or more input devices 2022 are connected to the interface circuit 2020. The input device(s) 2022 permit(s) a user to enter data and commands into the processor 2012. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 2024 are also connected to the interface circuit 2020 of the illustrated example. The output devices 2024 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 2020 of the illustrated example, thus, typically includes a graphics driver card, a graphics driver chip or a graphics driver processor.

The interface circuit 2020 of the illustrated example also includes a communication device such as a transmitter, a receiver, a transceiver, a modem and/or network interface card to facilitate exchange of data with external machines (e.g., computing devices of any kind) via a network 2026 (e.g., an Ethernet connection, a digital subscriber line (DSL), a telephone line, coaxial cable, a cellular telephone system, etc.).

The processor platform 2000 of the illustrated example also includes one or more mass storage devices 2028 for storing software and/or data. Examples of such mass storage devices 2028 include floppy disk drives, hard drive disks, compact disk drives, Blu-ray disk drives, RAID systems, and digital versatile disk (DVD) drives.

The coded instructions 2032 of FIG. 20 may be stored in the mass storage device 2028, in the volatile memory 2014, in the non-volatile memory 2016, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems, associated/included processors/computing devices, and resulting computer-aided prostate diagnosis using a plurality of deep learning and/or other machine learning techniques in conjunction with imaging data for a patient. Certain examples provide an automated and/or guided workflow and associated systems leveraging artificial intelligence networks and/or other systems to determine patient history, prostate gland volume, lesion identification and assessment, and recommendation/reporting. Certain examples associate a lesion with a sector map of a prostate and automate segmentation of the prostate gland and lesion. Artificial intelligence enables PIRADS and/or other scoring to develop a computer-assisted diagnosis and/or next action(s) in further diagnosis, treatment, reporting, triggering, etc. While MR reading time can be lengthy and difficult, certain examples automate MR image analysis and/or assist a user in evaluating relevant information emphasized in the image(s). Additionally, automated analyses can help to reduce an amount of unnecessary prostate biopsies while improving early detection, treatment, and monitoring of prostate issues.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A computer-aided prostate condition diagnosis apparatus comprising:
   a memory to store instructions; and
   a processor to execute the instructions to implement at least:
      a prostate assessor to evaluate a volume and density of a prostate gland in an image of a patient using distances deposited on the image to determine a prostate specific antigen level for the prostate gland;
      a lesion assessor to segment a lesion on the prostate gland in the image by depositing an ellipse on the lesion in the image, wherein the lesion assessor is to register the image including the deposited ellipse and a prostate sector map, wherein the lesion assessor is to automatically select one or more sectors corresponding to the ellipse on the segmented lesion, the one or more automatically selected sectors corresponding to a position of the ellipse in the registered prostate sector map, the prostate sector map comprising at least one of an axial plane, a sagittal plane, or a coronal plane, and wherein the lesion assessor is to determine a score representing an analysis of the segmented lesion; and
      an outcome generator to generate an assessment of prostate gland health based on the prostate-specific antigen level, the score representing the analysis of the segmented lesion, the prostate specific antigen level, the automatically selected one or more sectors, and the analysis of the segmented lesion applied to a machine learning model to generate a value for the assessment of prostate gland health.

2. The apparatus of claim 1, wherein the lesion assessor is to analyze the lesion using a plurality of scores to form a global score to classify the lesion.

3. The apparatus of claim 1, wherein the prostate assessor is to evaluate the volume and density of the prostate gland by segmenting and modeling the image using a deep learning network model.

4. The apparatus of claim 1, wherein the lesion assessor is to analyze the lesion by segmenting and modeling the image using a deep learning network model.

5. The apparatus of claim 1, wherein the lesion assessor is to overlay the ellipse on the lesion, the overlay of the ellipse to trigger the automatic selection of the one or more sectors underneath the ellipse in the image.

6. The apparatus of claim 1, wherein the image includes a three-dimensional volume.

7. The apparatus of claim 1, wherein the prostate assessor is to model the prostate gland with a digital twin.

8. A non-transitory computer-readable storage medium including instructions which, when executed, cause at least one processor to at least:
   evaluate a volume and density of a prostate gland in an image of a patient using distances deposited on the image to determine a prostate-specific antigen level for the prostate gland;
   segment a lesion on the prostate gland in the image by depositing an ellipse on the lesion in the image,
   register the image including the deposited ellipse and a prostate sector map,
   automatically select one or more sectors corresponding to the ellipse on the segmented lesion, the one or more automatically selected sectors corresponding to a position of the ellipse in the registered prostate sector map, the prostate sector map comprising at least one of an axial plane, a sagittal plane, or a coronal plane;
   determine a score representing an analysis of the segmented lesion; and
   generate an assessment of prostate gland health based on the prostate-specific antigen level, the score representing the analysis of the segmented lesion, the prostate-specific antigen level, the automatically selected one or more sectors, and the analysis of the segmented lesion applied to a machine learning model to generate a value for the assessment of prostate gland health.

9. The computer-readable storage medium of claim 8, wherein the instructions, when executed, cause the at least one processor to analyze the lesion using a plurality of scores to form a global score to classify the lesion.

10. The computer-readable storage medium of claim 8, wherein the instructions, when executed, cause the at least one processor to evaluate the volume and density of the prostate gland by segmenting and modeling the image using a deep learning network model.

11. The computer-readable storage medium of claim 8, wherein the instructions, when executed, cause the at least one processor to analyze the lesion by segmenting and modeling the image using a deep learning network model.

12. The computer-readable storage medium of claim 8, wherein the instructions, when executed, cause the at least one processor to overlay the ellipse on the lesion to trigger the automatic selection of the one or more sectors underneath the ellipse in the image.

13. The computer-readable storage medium of claim 8, wherein the image includes a three-dimensional volume.

14. The computer-readable storage medium of claim 8, wherein the instructions, when executed, cause the at least one processor to model the prostate gland with a digital twin.

15. A method for computer-aided prostate condition diagnosis, the method comprising:
   evaluating, with at least one processor, a volume and density of a prostate gland in an image of a patient using distances deposited on the image to determine a prostate specific antigen level for the prostate gland;
   segmenting, with the at least one processor, a lesion on the prostate gland in the image by depositing an ellipse on the lesion in the image;
   registering the image including the deposited ellipse and a prostate sector map,
   automatically selecting one or more sectors corresponding to the ellipse on the segmented lesion, the one or more sectors corresponding to a position of the ellipse in the registered prostate sector map, the prostate sector map comprising at least one of an axial plane, a sagittal plane, or a coronal plane;
   determining a score representing an analysis of the segmented lesion; and
   generating, with the at least one processor, an assessment of prostate gland health based on the prostate-specific antigen level, the score representing the analysis of the segmented lesion, the prostate specific antigen level, the automatically selected one or more sectors, and the analysis of the segmented lesion applied to a machine learning model to generate a value for the assessment of prostate gland health.

16. The method of claim 15, wherein analyzing the lesion includes analyzing the legion using a plurality of scores to form a global score to classify the lesion.

17. The method of claim 15, wherein evaluating the volume and density of the prostate gland includes evaluating the volume and density of the prostate gland by segmenting and modeling the image using a deep learning network model.

18. The method of claim 15, wherein analyzing the lesion includes analyzing the lesion by segmenting and modeling the image using a deep learning network model.

19. The method of claim 15, further including overlaying the ellipse on the lesion to trigger the automatic selection of the one or more sectors underneath the ellipse in the image.

20. The method of claim 15, wherein the image includes a three-dimensional volume.

* * * * *